(12) United States Patent
Wolf et al.

(10) Patent No.: US 8,980,411 B1
(45) Date of Patent: Mar. 17, 2015

(54) FOLDED ABSORBENT ARTICLE

(71) Applicant: Kimberly-Clark Worldwide, Inc., Neenah, WI (US)

(72) Inventors: Gay Lynn Wolf, Neenah, WI (US); Leila Joy Roberson, Kimberly, WI (US); Patsy Ann Benedict, Omro, WI (US); Brooke Ann Robaidek, Menash, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 32 days.

(21) Appl. No.: 14/014,678

(22) Filed: Aug. 30, 2013

(51) Int. Cl.
| | |
|---|---|
| *B32B 3/00* | (2006.01) |
| *B01J 20/28* | (2006.01) |
| *B01J 20/30* | (2006.01) |
| *B32B 3/16* | (2006.01) |
| *A61F 13/56* | (2006.01) |
| *A47C 31/10* | (2006.01) |

(52) U.S. Cl.
CPC .............. *B01J 20/2804* (2013.01); *B01J 20/30* (2013.01); *B32B 3/16* (2013.01); *A47C 31/105* (2013.01); *A61F 13/56* (2013.01); *C09J 2201/28* (2013.01)
USPC ..................... 428/198; 428/343; 5/487; 5/500

(58) Field of Classification Search
CPC ......... A61F 13/15; A61F 13/16; A61F 13/56; B32B 4/14; B32B 3/04; B32B 3/085; B32B 3/16; A47C 31/105
USPC .............. 428/198, 343; 5/484, 487, 498, 499, 5/500
See application file for complete search history.

(56) References Cited

U.S. PATENT DOCUMENTS

| | | | |
|---|---|---|---|
| 3,576,039 | A | 4/1971 | Roberts |
| 4,097,943 | A | 7/1978 | O'Connell |
| 4,522,624 | A | 6/1985 | Bolick |
| 4,536,433 | A | 8/1985 | Sagi et al. |
| 5,068,936 | A | 12/1991 | Blitzer |
| 6,524,289 | B1 | 2/2003 | Larsson et al. |
| 6,911,407 | B2 | 6/2005 | Sherrod et al. |
| D597,357 | S | 8/2009 | Stewart |
| 7,754,327 | B2 | 7/2010 | Kong |
| D655,556 | S | 3/2012 | Isom-Morris |
| 2004/0060112 | A1 | 4/2004 | Fell et al. |
| 2007/0255243 | A1 | 11/2007 | Kaun et al. |

FOREIGN PATENT DOCUMENTS

| | | | |
|---|---|---|---|
| EP | 0 218 568 B1 | 4/1990 | |
| EP | 0 499 571 A1 | 8/1992 | |

*Primary Examiner* — Elizabeth Mulvaney
(74) *Attorney, Agent, or Firm* — Kimberly-Clark Worldwide, Inc.

(57) ABSTRACT

A method of making a folded absorbent article includes the steps of: providing an absorbent structure; providing a liquid-impermeable back sheet having a body-facing surface and a substrate-facing surface; joining the absorbent structure in facing relation to the body-facing surface of the back sheet to define an absorbent article; applying adhesive to the substrate-facing surface of the back sheet to define a first adhesive zone and a second adhesive zone; treating portions of the substrate-facing surface of the back sheet to define a first treated zone and a second treated zone; folding the absorbent article to align the first adhesive zone in facing relation with the first treated zone; and folding the absorbent article to align the second adhesive zone in facing relation with the second treated zone.

20 Claims, 18 Drawing Sheets

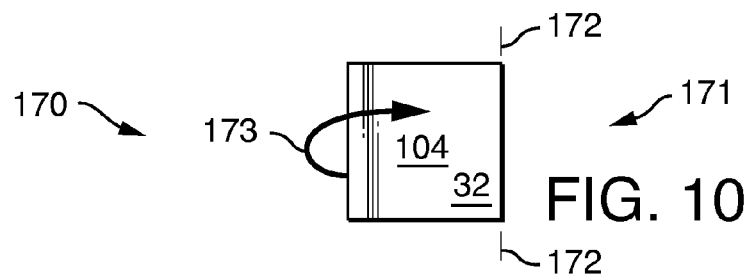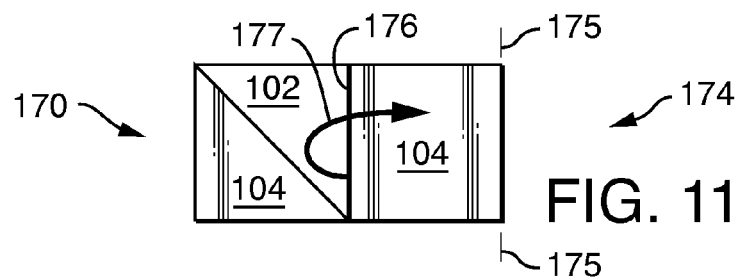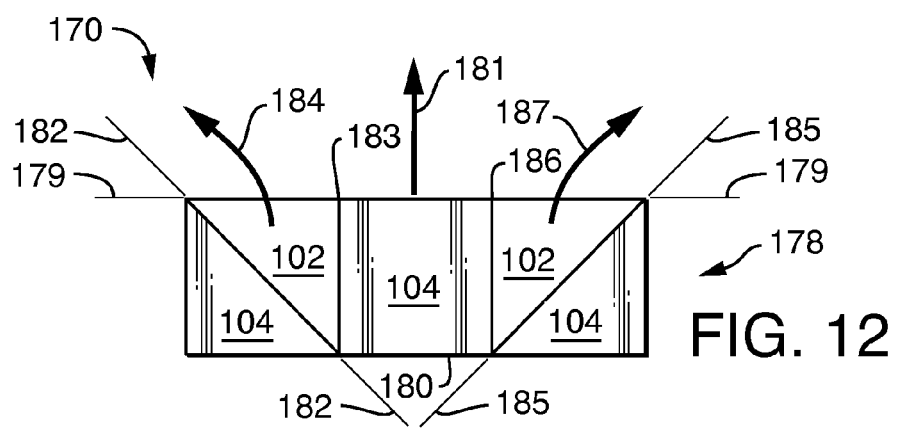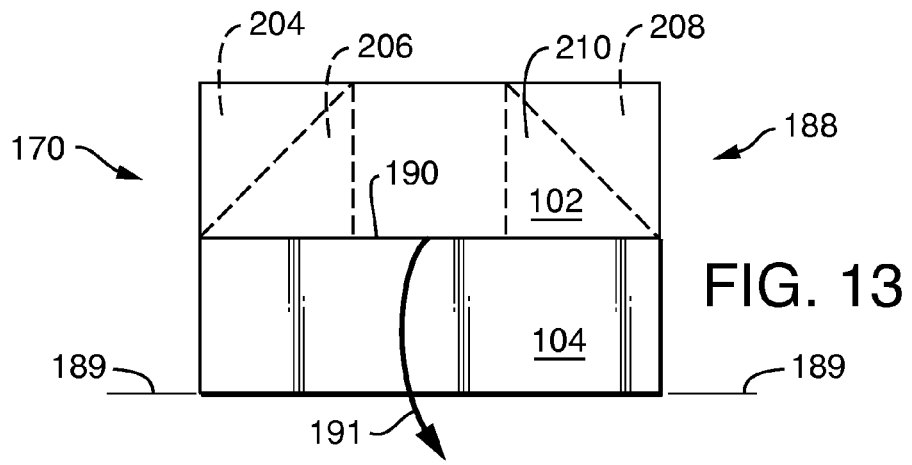

FOLDED ABSORBENT ARTICLE

BACKGROUND OF THE INVENTION

The present invention relates generally to disposable absorbent articles for absorbing fluids and more particularly to a disposable absorbent article having adhesive for adhering the article to a substrate. While disposable absorbent articles are known to protect mattresses, linens, furniture, and the like from body fluids, there remains a need for a disposable absorbent article that adheres to various surfaces but requires no release sheet.

SUMMARY OF THE INVENTION

In one aspect, the present invention provides an absorbent article having a back sheet and an absorbent structure wherein the back sheet has a body-facing surface and a substrate-facing surface and wherein the absorbent structure is joined in facing relation with the body-facing surface of the back sheet to define the absorbent article. The substrate-facing surface of the back sheet also includes an adhesive zone and a treated zone. The absorbent article is folded along a fold line such that the adhesive zone and the treated zone are aligned in facing relation.

In various embodiments, the absorbent article defines a longitudinal direction and a lateral direction perpendicular to the longitudinal direction and the fold line is parallel with either the lateral direction or the longitudinal direction. In some embodiments, the fold line is non-parallel with either the lateral direction or the longitudinal direction. In some embodiments, the absorbent article includes a fold line that is parallel with the lateral direction and/or the longitudinal direction and also includes a fold line that is non-parallel with either the lateral direction or the longitudinal direction.

In various embodiments, the back sheet includes a first adhesive zone, a second adhesive zone, a first treated zone, and a second treated zone each positioned on the substrate-facing surface. The absorbent article is folded along a first fold line such that the first adhesive zone and the first treated zone are aligned in facing relation. The absorbent article is also folded along a second fold line such that the second adhesive zone and the second treated zone are aligned in facing relation. In some embodiments, the absorbent article is folded at a third fold line to define a folded configuration having complete protection of the body-facing surface (i.e., the protected condition). In some embodiments, the absorbent article is folded at a third fold line to define a folded configuration having complete protection of the first adhesive zone and the second adhesive zone.

In various embodiments, the first adhesive zone and the second adhesive zone include pressure sensitive adhesive that has been applied in a slot coat pattern. In some embodiments, the first treated zone and the second treated zone include silicone that has been applied in a spray pattern.

In various embodiments, the back sheet includes a first adhesive zone, a second adhesive zone, a third adhesive zone, a fourth adhesive zone, a first treated zone, a second treated zone, a third treated zone, and a fourth treated zone, each on the substrate-facing surface. In these embodiments, the absorbent article is folded along a first fold line such that the first adhesive zone and the first treated zone are aligned in facing relation and the second adhesive zone and the second treated zone are aligned in facing relation. Additionally, the absorbent article is folded along a second fold line such that the third adhesive zone and the third treated zone are aligned in facing relation and the fourth adhesive zone and the fourth treated zone are aligned in facing relation.

In another aspect, the present invention provides a method of making a folded absorbent article. The method includes providing an absorbent structure, providing a liquid-impermeable back sheet having a body-facing surface and a substrate-facing surface, and joining the absorbent structure in facing relation to the body-facing surface of the back sheet to define an absorbent article. The method further includes the step of applying adhesive to the substrate-facing surface of the back sheet to define a first adhesive zone and a second adhesive zone. The method further includes the step of treating portions of the substrate-facing surface of the back sheet to define a first treated zone and a second treated zone. The method further includes the steps of folding the absorbent article to align the first adhesive zone in facing relation with the first treated zone and folding the absorbent article to align the second adhesive zone in facing relation with the second treated zone.

In various embodiments, the method may further include the step of folding the absorbent article to define a protected condition wherein only the substrate-facing surface is exposed. In some embodiments, the method further includes repeating these steps to provide a plurality of absorbent articles in the protected condition and placing the plurality of absorbent articles into a package while in the protected condition.

In various embodiments, the treating step includes applying silicone to the substrate-facing surface of the back sheet to define the first treated zone and the second treated zone.

In various embodiments, the absorbent article defines a longitudinal direction and a lateral direction and the folding step of the method further includes folding the absorbent article along a first line that is parallel to the longitudinal direction or folding the absorbent article along a second line that is parallel to the lateral direction.

In various embodiments, the absorbent article defines a longitudinal direction and a lateral direction and the folding step of the method further includes folding the absorbent article along a first line that is neither parallel to the longitudinal direction nor the lateral direction.

In another aspect, the present invention provides a method of making a folded absorbent article. The method includes providing an absorbent structure, providing a liquid-impermeable back sheet made of polyethylene film and having a body-facing surface and a substrate-facing surface, and providing a top sheet made of non-woven spunbond polymer. The method further includes joining the absorbent structure in facing relation to the body-facing surface of the back sheet to define an absorbent article. The method further includes applying adhesive to the substrate-facing surface of the back sheet to define a first adhesive zone, a second adhesive zone, a third adhesive zone, and a fourth adhesive zone. The method also includes treating portions of the substrate-facing surface of the back sheet with silicone to define a first treated zone, a second treated zone, a third treated zone, and a fourth treated zone.

The method further includes folding the absorbent article to align the first adhesive zone in facing relation with the first treated zone, folding the absorbent article to align the second adhesive zone in facing relation with the second treated zone, folding the absorbent article to align the third adhesive zone in facing relation with the third treated zone, and folding the absorbent article to align the fourth adhesive zone in facing relation with the fourth treated zone. The method also includes the step of folding the absorbent article to define a protected condition wherein only the substrate-facing surface is exposed.

In some embodiments, the absorbent article defines a longitudinal direction and a lateral direction and the folding step includes folding the absorbent article along a first line that is parallel to the longitudinal direction or folding the absorbent article along a second line that is parallel to the lateral direction.

In some embodiments, the folding step includes folding the absorbent article along a first line that is neither parallel to the longitudinal direction nor the lateral direction.

BRIEF DESCRIPTION OF THE DRAWINGS

FIG. 10 is a top view of another exemplary absorbent article in a first folded configuration.

FIG. 11 is a top view of the absorbent article of FIG. 10 in a second folded configuration.

FIG. 12 is a top view of the absorbent article of FIG. 10 in a third folded configuration.

FIG. 13 is a top view of the absorbent article of FIG. 10 in a fourth folded configuration.

DETAILED DESCRIPTION OF THE DRAWINGS

Figure 1:
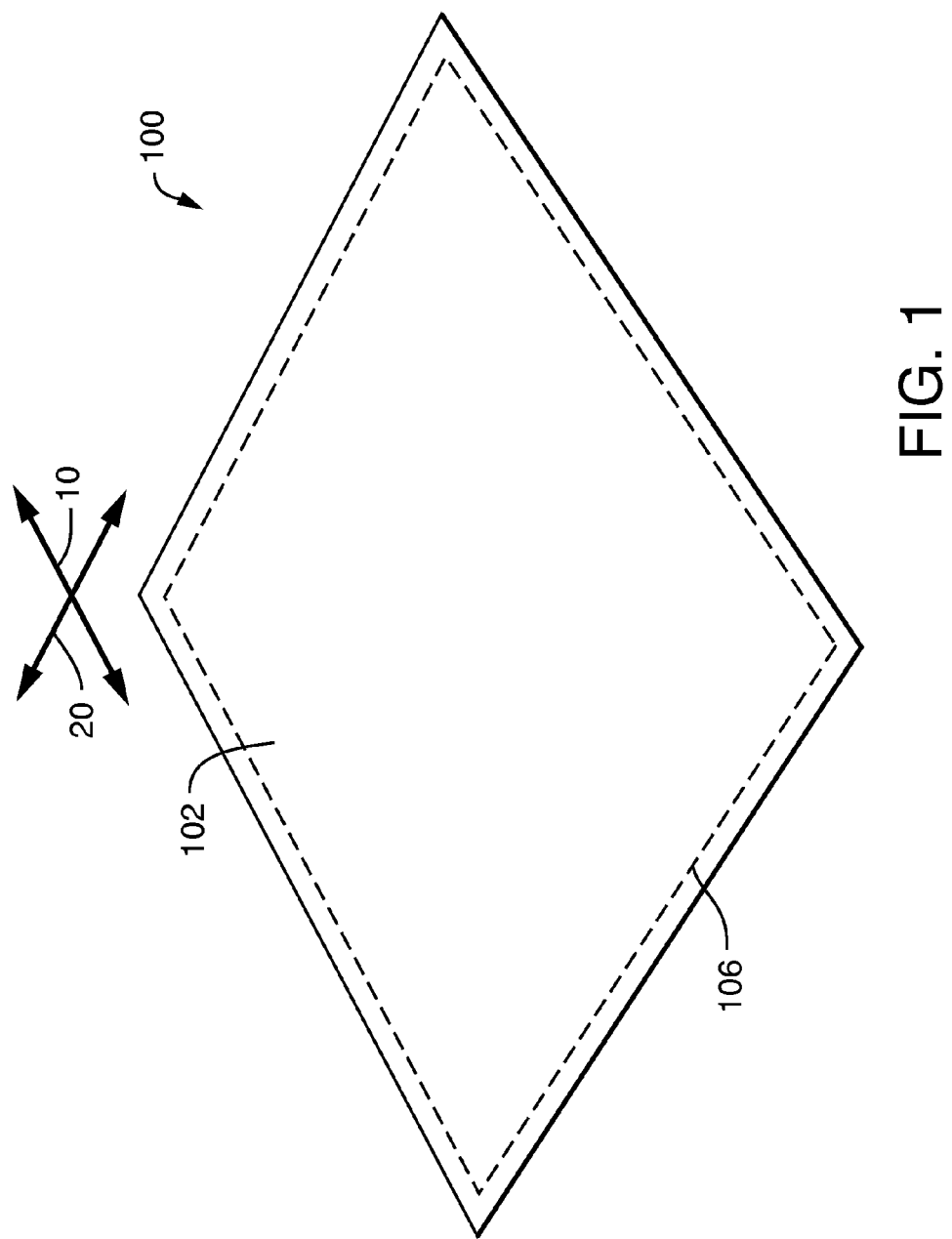
FIG. 1 is a perspective view of an exemplary disposable absorbent.
Figure 2:
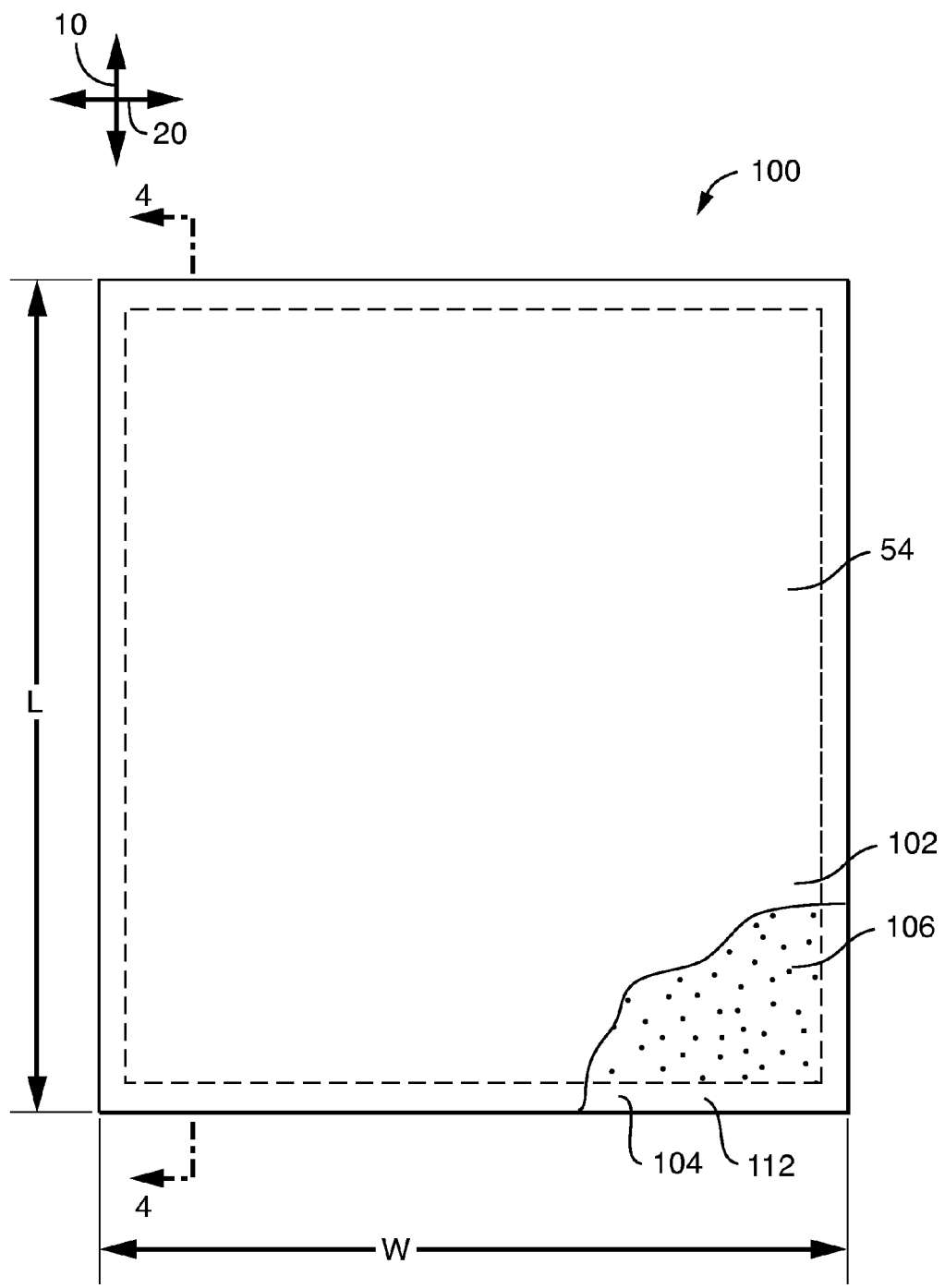
FIG. 2 is a top view of the disposable absorbent article of FIG. 1 with the body-facing surface towards the viewer and with a portion of the top sheet cut away to illustrate the underlying structure.
Figure 3:
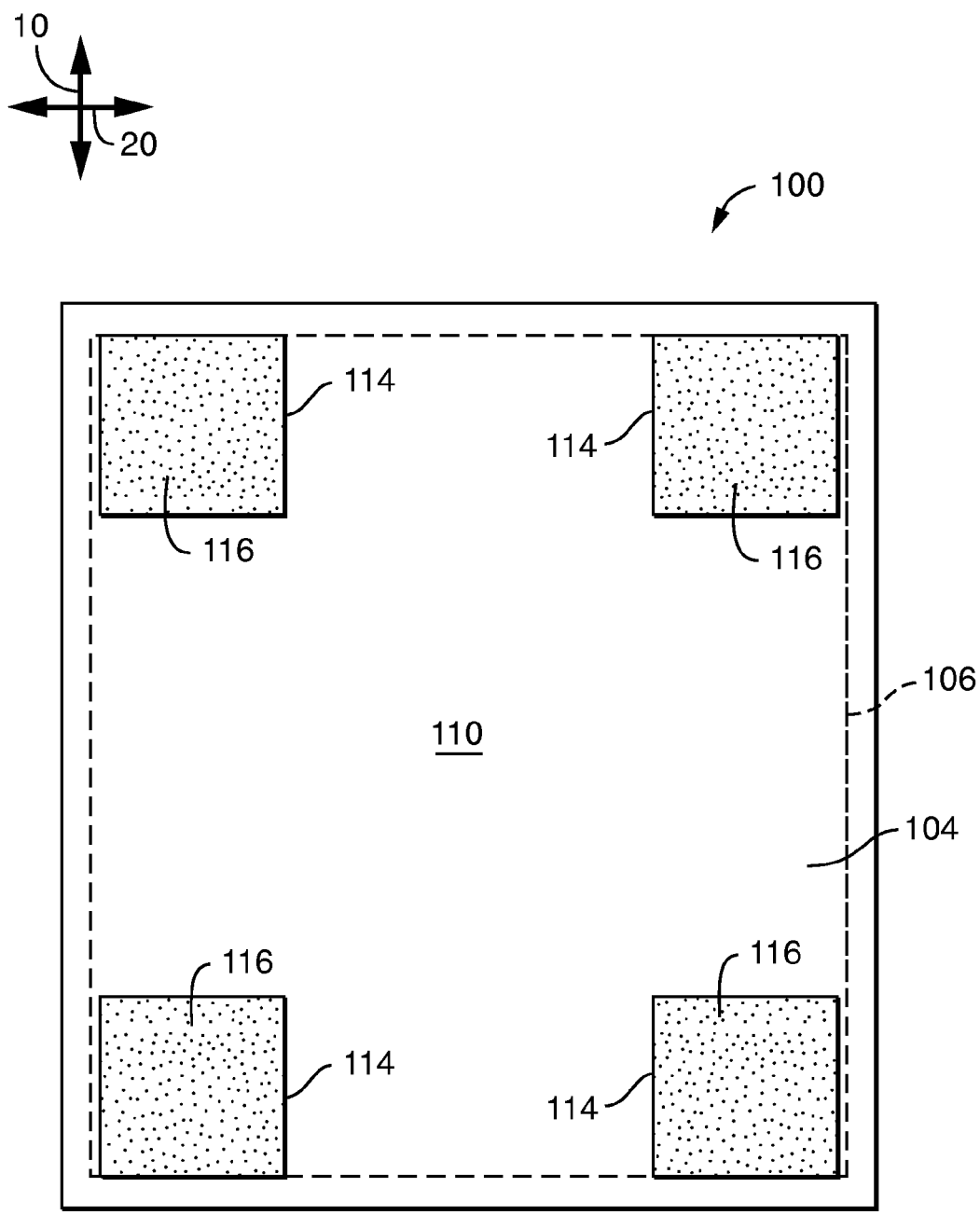
FIG. 3 is a bottom view of the disposable absorbent article of FIG. 1 with the substrate-facing surface towards the viewer.
Figure 4:
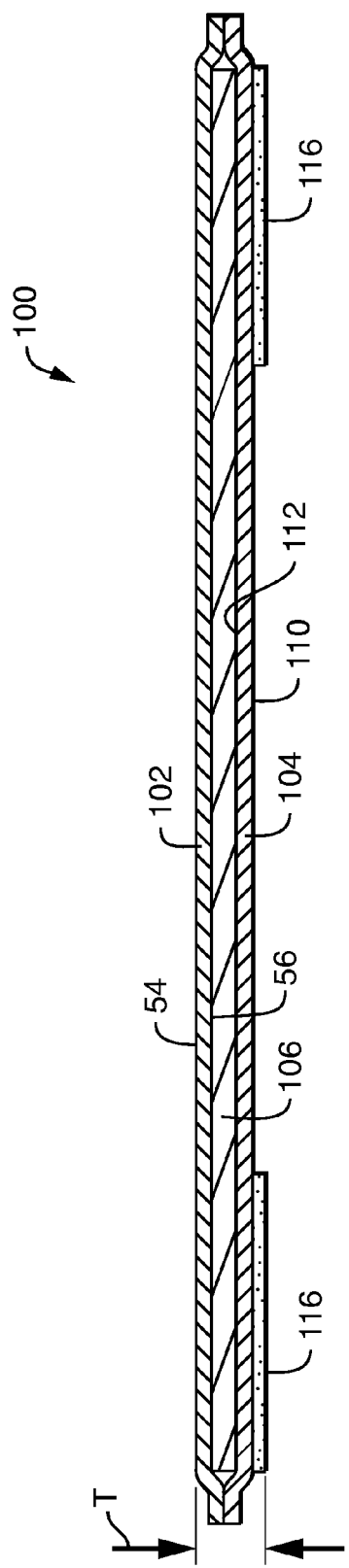
FIG. 4 is a cross-section view of the absorbent article of FIG. 2 taken along line 4-4.
Figure 5:
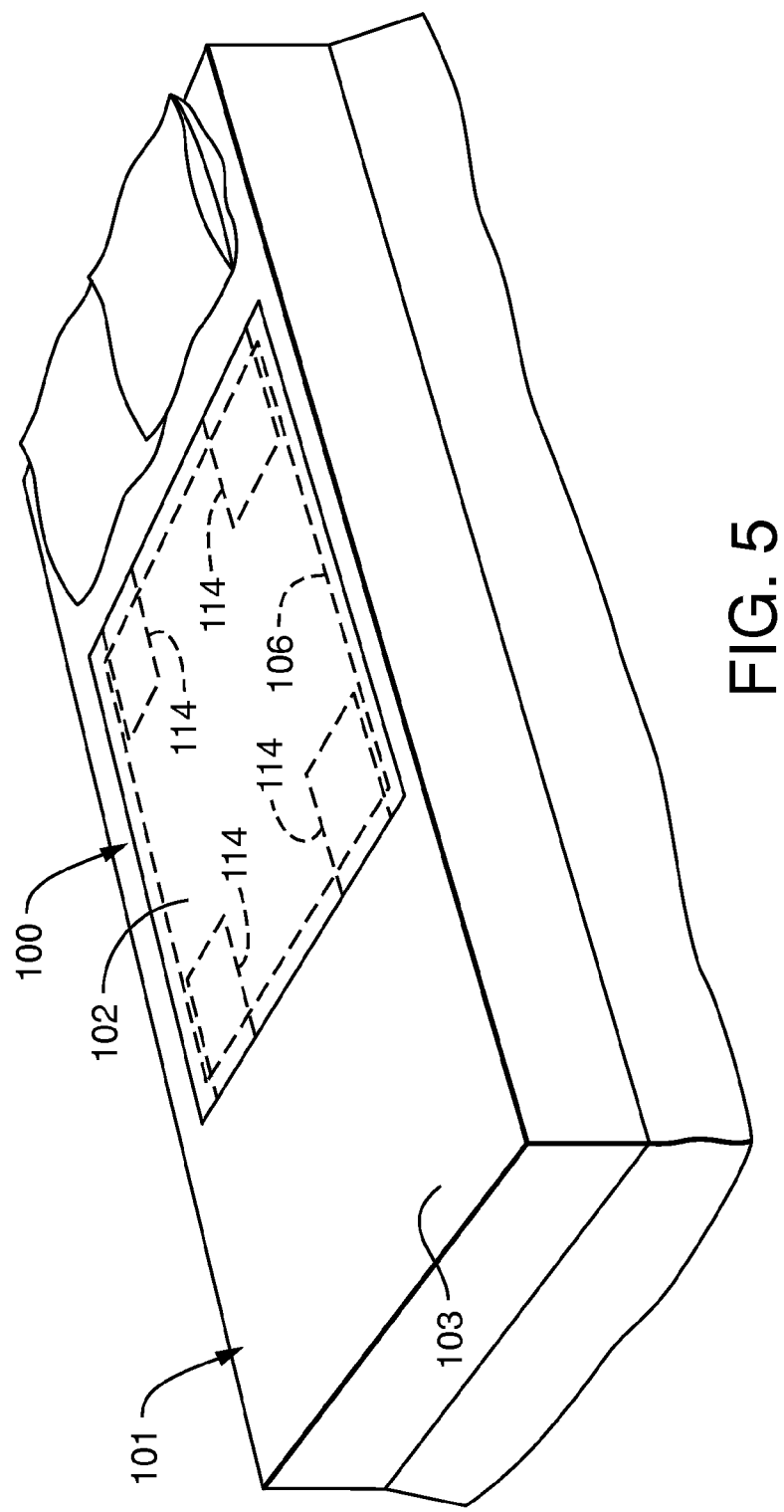
FIG. 5 is a perspective view of the disposable absorbent article of FIG. 1 placed on a bed and attached to a bottom sheet thereof.

FIGS. 1-5 illustrate an exemplary disposable absorbent article 100 configured to absorb fluid, such as bodily fluid. FIG. 1 is a perspective view of the disposable absorbent article 100 with the body-facing surface towards the viewer. FIG. 2 is a top view of the disposable absorbent article 100 of FIG. 1 with the body-facing surface towards the viewer and with a portion of the top sheet cut away to illustrate the underlying structure. FIG. 3 is a bottom view of the disposable absorbent article 100 of FIG. 1 with the substrate-facing surface towards the viewer. FIG. 4 is a cross-section view of the absorbent article 100 of FIG. 2 taken along the line 4-4. FIG. 5 is a perspective view of the disposable absorbent article 100 of FIG. 1 placed on a bed and attached to a bottom sheet thereof. Other suitable absorbent articles are described in U.S. publication 20130115437, Ser. No. 13/291,871, filed on Nov. 8, 2011, the entirety of which is incorporated herein by reference where not contradictory.

The illustrated disposable absorbent article 100 is sized and shaped for placing on a bed 101 (FIG. 5). More specifically, the illustrated disposable absorbent article 100 is adapted to be adhered to a bottom (e.g., a fitted) sheet 103 of the bed and underlie a child sleeping in the bed. Thus, as described in more detail below, the disposable absorbent article 100 inhibits bodily fluid (e.g., urine) released from the child while sleeping in the bed 101 from wetting the bed sheet 103 or a mattress of the bed. In various embodiments, the disposable absorbent article 100 may be placed between the bed sheet 103 and the mattress of the bed 101. In such a configuration, the disposable absorbent article 100 can be adhered directly to the mattress. In various embodiments, the disposable absorbent articles described herein may be used to protect any suitable surface from contact with fluids. For example, the disposable absorbent articles described herein may be used to protect furniture, flooring, automobile fabric, and the like from contact with various fluids. In various embodiments, the disposable absorbent articles may be used to absorb any suitable bodily fluids and other types of fluids (e.g., spilled drinks). In various embodiments, the disposable absorbent articles may be used for individuals besides children including, but not limited to, infants, elderly, and the bedridden. In addition, in various embodiments, the disposable absorbent articles may be used for pets.

The disposable absorbent articles of the present invention have a longitudinal direction 10 and a lateral direction 20. The illustrated disposable absorbent article 100, for example, has a length L (i.e., the extent of the disposable absorbent article in the longitudinal direction 10) of approximately 880 millimeters and a width W (i.e., the extent of the disposable absorbent article in the lateral direction 20) of approximately 780 millimeters. Thus, the illustrated disposable absorbent article 100 is generally rectangular. In various embodiments, the articles can have any suitable length and/or width. In some embodiments, the length of the disposable absorbent articles described herein can range from about 12 inches (305 millimeters) to about 84 inches (2,135 millimeters), and the width of the disposable absorbent articles can range from about 12 inches (305 millimeters) to about 72 inches (1,829 millimeters). In various embodiments, the disposable absorbent articles can have any suitable shape (e.g., square, circular, elliptical).

In some embodiments, the absorbent articles include a top sheet 102, a back sheet 104 and an absorbent structure 106 disposed between the top sheet and the back sheet. In general, the absorbent articles define a body-facing surface 30 and a substrate-facing surface 32. In the illustrated embodiments, the exposed surface of the top sheet 102 defines the body-facing surface 30 of the absorbent article. Likewise, in the illustrated embodiments, the exposed surface of the back sheet 104 defines the substrate-facing surface 32 of the absorbent article.

In the illustrated embodiments, the top sheet 102 and back sheet 104 extend beyond the periphery of the absorbent structure 106 and are adhesively bonded to each other to capture the absorbent structure. In various embodiments, the top sheet and the back sheet may be bonded together about the periphery of the absorbent structure using any suitable bonding technique. In some embodiments, the top sheet, the back sheet, and the absorbent structure may be coextensive. In some embodiments, the absorbent structure may extend beyond the top sheet and/or the back sheet.

In various embodiments, the absorbent structure 106 may be adhesively bonded to both the top sheet 102 and the back sheet 104. In addition, the top sheet 102 may be adhesively bonded to the back sheet 104 about the periphery of the absorbent structure 106. In various embodiments, the top sheet 102, the back sheet 104, and/or the absorbent structure 106 may be bonded together using other suitable bonding techniques in addition to or in place of adhesive. In some embodiments, the top sheet 102 may be free from direct bonding with either the back sheet 104 or the absorbent structure 106, or the back sheet may be free from direct bonding with either the top sheet or the absorbent structure.

One suitable way to form the illustrated disposable absorbent articles includes placing the discrete absorbent structure 106 on a continuous web to which adhesive has been uniformly applied. In some embodiments, the continuous web may be the back sheet 104. Next, a continuous web of nonwoven material (or other material suitable for use as the top sheet 102), which has adhesive applied thereto, may be laid over the absorbent structure 106. The resulting laminate structure may then be passed through a suitable nip (e.g., a rubber/steel nip) to assure pad integrity.

The absorbent structure 106 is configured to absorb body fluids including, but not limited to, urine that passes through the top sheet 102. The absorbent structure 106 may have one or more layers of absorbent materials. That is, the absorbent structures 106 may be a single layer of absorbent materials or may be a multilayer structure. Each of the layers of the absorbent structure 106 can contain similar materials or different materials.

Suitable materials which can be used to form the absorbent structure 106 include those materials conventionally used in absorbent articles and include materials, such as, for example, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose.

The absorbent structure 106 of the various embodiments can also be formed from a composite comprised of a hydrophilic material which may be formed from various natural or synthetic fibers, wood pulp fibers, regenerated cellulose or cotton fibers, or a blend of pulp and other fibers. One particular example of a material which may be used as the absorbent structure is an airlaid material.

In some embodiments, the absorbent structures 106 may include a superabsorbent material, in addition to or in place of the hydrophilic material, which increases the ability of the absorbent structure to absorb a large amount of fluid in relation to its own weight. Generally stated, the superabsorbent material can be a water-swellable, generally water-insoluble, hydrogel-forming polymeric absorbent material, which is capable of absorbing at least about 15, suitably about 30, and possibly about 60 times or more its weight in physiological saline (e.g., saline with 0.9 wt % NaCl). The superabsorbent materials can be inserted into the absorbent structure 106 as particles or in sheet form. The superabsorbent material may be biodegradable or bipolar. In various embodiments, the superabsorbent material may be uniformly distributed or selectively placed within the absorbent structure 106. The amount of superabsorbent material may be selected to hold an anticipated quantity of liquid such as urine, for instance during over-night usage. The amount of superabsorbent material may, for example, be from about 5 grams to about 100 grams of a highly absorbent polyacrylate.

The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking bonds may, for example, be by irradiation or covalent, ionic, Van der Waals, hydrogen bonding, or combinations thereof. Hydroxyfunctional polymers have been found to be good superabsorbents for sanitary napkins. Such superabsorbents are commercially available from Dow Chemical, Hoechst-Celanese, and Stockhausen, Incorporated, among others, and are a partially neutralized salt of cross-linked copolymer of polyacrylic acid and polyvinyl alcohol having an absorbency under load value above 25 grams of absorbed liquid per gram of absorbent material (g/g). Other types of superabsorbent materials known to those skilled in the art can also be used.

The absorbent structure 106 of the various embodiments may include pattern bonding defined by a plurality of bonds. The bonds may have any suitable size and/or shape and may be arranged in any suitable pattern. In one suitable embodiment, the bonds may be circular and have a diameter of less than about 10 millimeters and suitably, between about 0.5 millimeters and about 3 millimeters. In one suitable embodiment, more than 1 percent of the absorbent structure 106 is bonded by the point bonds. Suitably, 10 percent to 60 percent of the absorbent structure 106 is bonded by the point bonds. More suitably, 15 percent to 45 percent of the absorbent structure 106 is bonded by the point bonds. In one suitable embodiment, for example, approximately 17.5 percent of the absorbent structure 106 is bonded by the point bonds.

It is understood that the pattern bonding can be formed using any suitable pattern including continuous and discontinuous patterns. For example, the pattern bonding can comprise the discontinuous point bonds or can include a continuous line diamond pattern. It is also understood that the pattern bonding can be in the form of a decorative figure, e.g., an animal, a cartoon character, or other playful character. It is contemplated that the pattern bonding could be achieved in any suitable manner including heated rollers, ambient temperature rollers, or ultrasonic bonding.

In some embodiments, the absorbent structure 106 can be made by distributing cellulose fluff uniformly onto a tissue paper layer. Next, particles of suitable super absorbent material (SAM) are generally uniformly distributed onto the fluff. Then another layer of tissue paper is placed over the cellulose fluff containing the SAM to form a composite. The composite is then compacted using any suitable means. In one example, the composite can be passed through a steel/steel nip. In one suitable embodiment, the steel/steel nip comprises an embossing roll and an associated anvil roll. Suitably, either the embossing roll or the anvil roll is heated and, more suitably, both the embossing roll and the anvil roll are heated.

It is contemplated that the absorbent structures 106 can be formed as a continuous web or as discrete units. If the absorbent structures 106 are formed as a continuous web comprising a plurality of interconnected absorbent structures, the method of forming the absorbent structures could include a suitable device to cut the interconnected absorbent structure into discrete piece. For example, one suitable cutting device is a knife and an associated anvil roll.

In various embodiments, the top sheet 102 may comprise a liquid permeable material, which allows fluids to pass through the top sheet and into the underling absorbent structure 106. In some embodiments, the top sheet 102 can be adapted to direct bodily fluids (e.g., urine) away from the user and toward the absorbent structure 106. That is, the top sheet 102 can be configured to retain little to no fluid in its structure and readily allow body fluids to pass there through. Suitably, the top sheet 102 can be configured to provide a relatively comfortable and non-irritating surface for the user.

The top sheet 102 can include a layer constructed of any operative material, and may be a composite material. For example, the top sheet 102 can include a woven fabric, a nonwoven fabric, a polymer film, a film-nonwoven fabric laminate or the like, as well as combinations thereof. Examples of a nonwoven fabric useable in the top sheet 102 include, for example, an airlaid nonwoven web, a spunbond nonwoven web, a meltblown nonwoven web, a bonded-carded web, a hydroentangled nonwoven web, a spunlace web or the like, as well as combinations thereof. Other examples of suitable materials for constructing the top sheet 102 can include rayon, bonded-carded webs of polyester, polypropylene, polyethylene, nylon, or other heat-bondable fibers, finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat-bondable materials. When the top sheet 102 is a film or a film laminate, the film may be sufficiently apertured or otherwise worked to allow fluids to flow through the top sheet to the absorbent structure 106.

Other examples of suitable materials for the top sheet 102 are composite materials of a polymer and a nonwoven fabric material. The composite materials are typically in the form of integral sheets generally formed by the extrusion of a polymer onto a nonwoven web, such as a spunbond material. In a particular arrangement, the top sheet 102 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, that are present or formed in the top sheet 102. The apertures or other openings can help increase the rate at which bodily fluid (e.g., urine) can move through the thickness of the top sheet 102 and penetrate into the absorbent structure 106.

In the illustrated embodiments, the top sheet 102 extends beyond the absorbent structure 106 and is adhesively bonded to the back sheet 104. It is contemplated, however, that the top sheet 102 can have the same extent as the absorbent structure 106 and/or back sheet 104 or can have an extent less than the absorbent structure and/or back sheet. It is further contemplated that in some embodiments (not shown), the top sheet 102 can be omitted. Thus, in such an embodiment, the disposable absorbent article 100 would comprise only the absorbent structure 106 and the back sheet 104.

Additional layers or substrates, such as, a liquid acquisition and distribution layer, also referred to as a surge or transfer layer, and an optional tissue layer can be incorporated into the absorbent structure 106 of the absorbent articles. The distribution layer may be shorter than the absorbent structure 106 or have the same length as the absorbent structure. The distribution layer serves to temporarily hold an insulting fluid to allow the absorbent structure sufficient time to absorb the fluid, especially when a superabsorbent material is present.

The back sheet 104 of the various embodiments is generally liquid impermeable and is attached to the absorbent structure 106 to prevent fluid entering the absorbent structure 106 from flowing through the absorbent structure and onto the substrate (e.g., bed sheet 103 of FIG. 5) to which the disposable absorbent articles are adhered. More specifically, the back sheet 104 has a substrate-facing surface 110 and an opposing body-facing surface 112. As illustrated in FIG. 4, the absorbent structure 106 is attached (e.g., adhesively bonded) to the body-facing surface 112 of the back sheet 104. It is understood that the substrate to which the disposable absorbent article is adhered can be any suitable substrate including, but not limited to, bed sheets (cotton, fleece, cotton/synthetic fiber blends, bamboo), mattresses, bed mats, chairs, sofas, car seats, and floors (carpet, vinyl covering, wood flooring).

The liquid impermeable back sheet 104 may be a polymeric film, a woven fabric, a nonwoven fabric or the like, as well as combinations or composites thereof. For example, the liquid impermeable back sheet 104 may include a polymer film laminated to a woven or nonwoven fabric. The polymer film can be composed of polyethylene, polypropylene, polyester, or the like, as well as combinations thereof. Additionally, the polymer film may be micro-embossed, have a printed design, have a printed message to the consumer, and/or may be at least partially colored.

The back sheet 104 may be made from a liquid/moisture permeable material that is rendered moisture proof by means of hydrophobic additives. It is understood that the back sheet 104 can be made from a fibrous (e.g., a nonwoven) material or other suitable permeable material. In such an embodiment, the disposable absorbent article may include a suitable barrier layer.

In various embodiments, the substrate-facing surface 110 of the back sheet 104 also includes at least one zone 114 having adhesive 116 applied thereto. For example, referring now to FIG. 3, the substrate-facing surface 110 of the back sheet 104 includes four zones 114 having adhesive 116 applied thereto. As seen in FIG. 3, each of the four zones 114 is positioned generally adjacent the corners of the substrate-facing surface 110 of the back sheet 104. It is contemplated that the substrate-facing surface 110 of the back sheet 104 can have more or fewer zones 114 of adhesive 116 than the four zones of adhesive illustrated in FIG. 3. It is also contemplated that the adhesive 116 can be applied to other portions of the substrate-facing surface 110. Thus, the adhesive 116 can be applied to portions of the substrate-facing surface 110 spaced from its corners.

In various embodiments, the adhesive 116 covers about 5-100 percent, about 10-60 percent, or about 10-40 percent of the substrate-facing surface 110 of the back sheet 104. In some embodiments, the adhesive may cover about 16 percent of the substrate-facing surface 110 of the back sheet 104.

In various embodiments, the adhesive 116 is applied to the substrate-facing surface 110 of the back sheet 104 in a range between about 10 grams per square meter (gsm) and about 60 gsm. Suitably, approximately 40±5 gsm of adhesive 116 is applied to the substrate-facing surface 110 of the back sheet 104. It is understood, however, that the quantity of adhesive 116 applied to the back sheet 104 can differ from those disclosed herein. Rather, any suitable quantity of adhesive 116 can be applied to the substrate-facing surface 110 of the back sheet 104.

Figure 16:
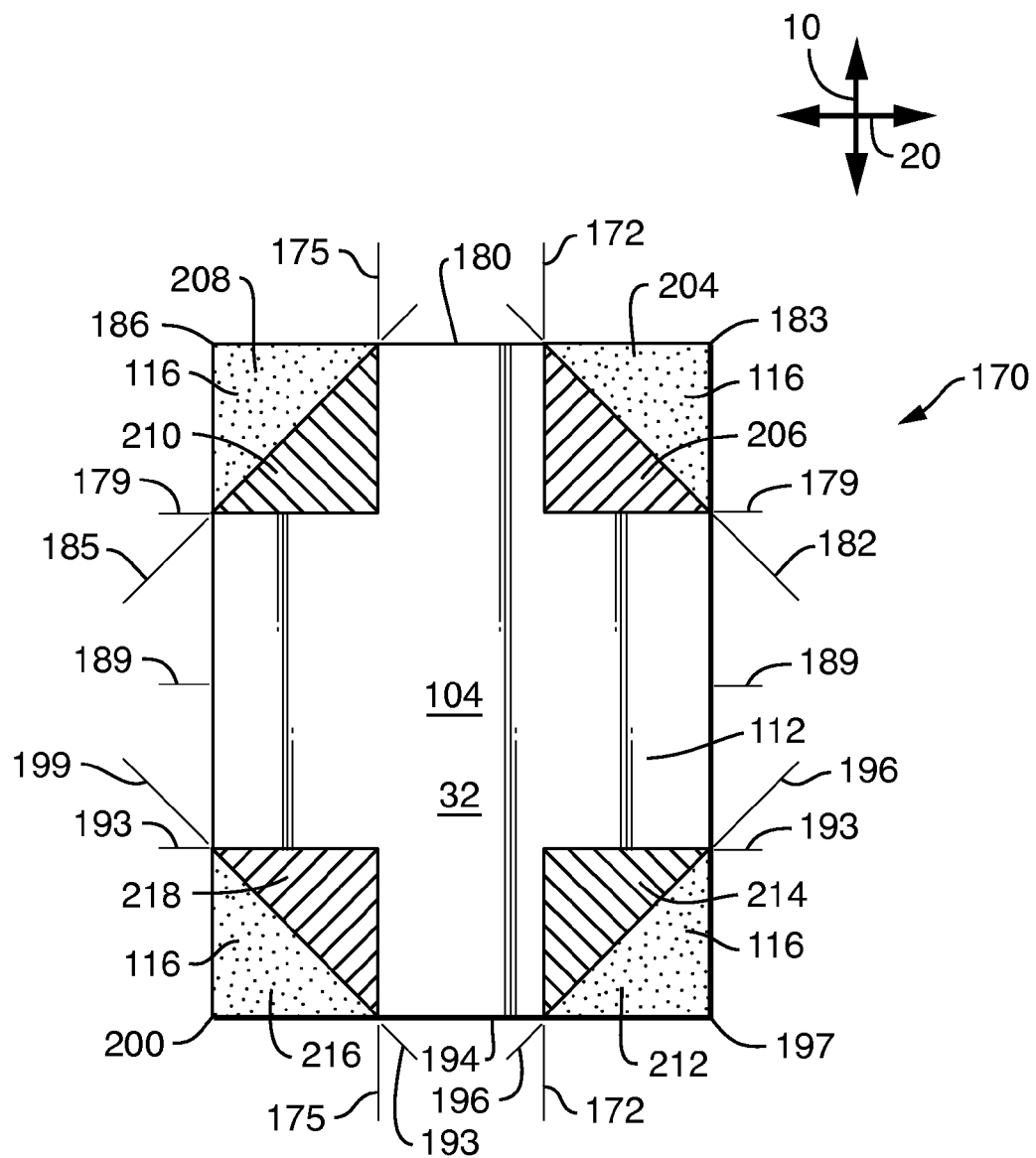
FIG. 16 is a bottom view of the absorbent article of FIG. 10 in an unfolded configuration with the substrate-facing surface towards the viewer.
Figure 22:
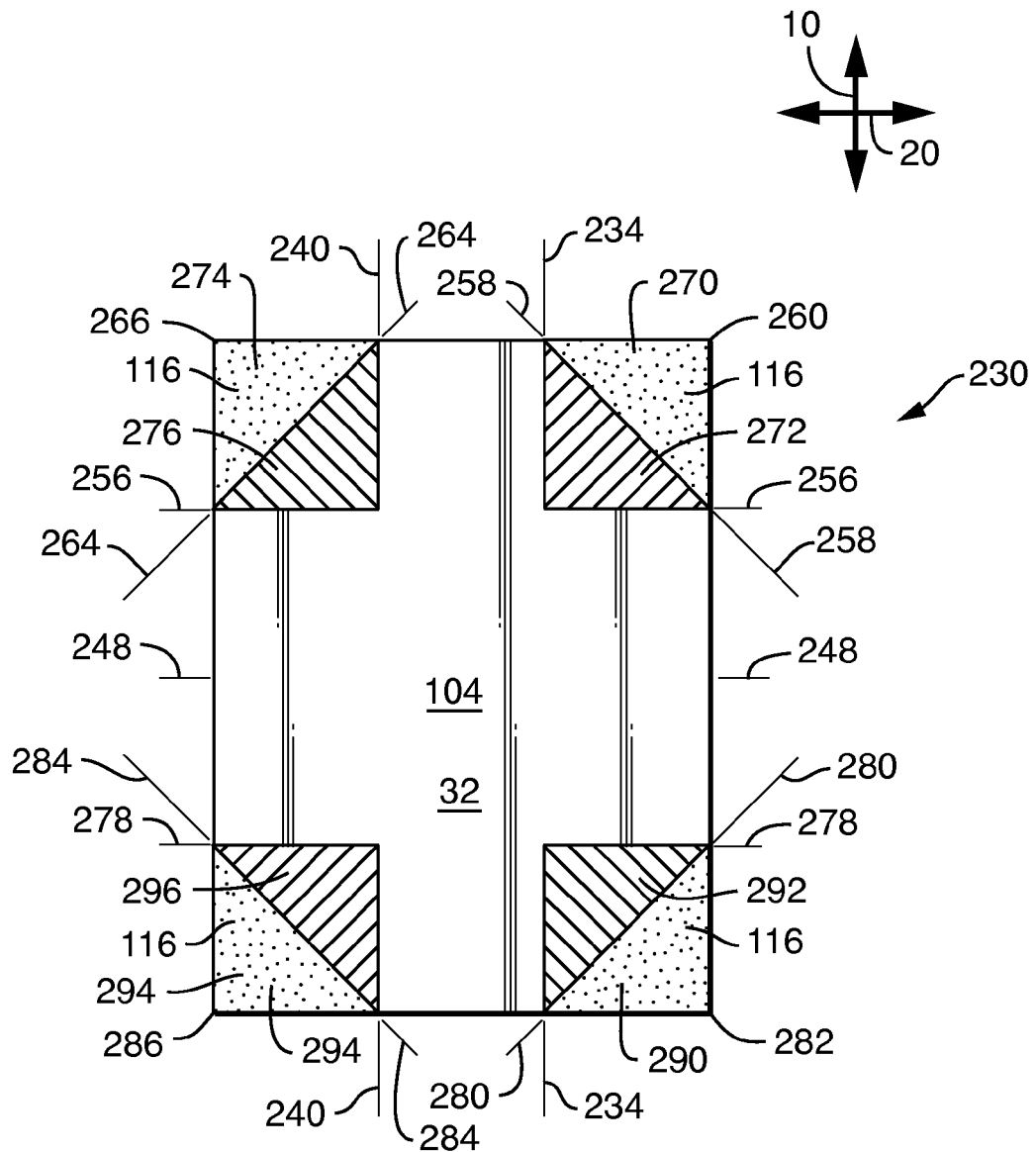
FIG. 22 is a bottom view of the absorbent article of FIG. 17 in an unfolded configuration with the substrate-facing surface towards the viewer.

In some embodiments, each zone 114 of adhesive 116 has a substantially rectangular shape as illustrated in FIG. 3. It is contemplated, however, that each of the zones 114 of adhesive 116 may have any suitable shape and/or size. For example, in some embodiments, each zone 114 of adhesive 116 has a substantially triangular shape as illustrated in FIGS. 16 and 22. It is also contemplated that the adhesive 116 can be applied to the substrate-facing surface 110 of the back sheet 104 in any suitable pattern (e.g., strips, dots).

In various embodiments, the adhesive 116 is an adhesive that enables the disposable absorbent article 100 to be removably attached to the bed sheet 103. That is, the adhesive 116 enables the disposable absorbent article 100 to be held in place on the bed sheet 103 during use and the disposable absorbent article may be readily removed from the bed sheet after use. Suitably, little or no residual adhesive 116 will remain on the bed sheet 103 after the disposable absorbent article 100 is removed therefrom. It is also preferred that the adhesive 116 does not permanently or temporarily mark or otherwise discolor the bed sheet 103. Several suitable adhesives are available from HB Fuller with an office in St. Paul, Minn., U.S.A. and available under product numbers 1827S and CHM1056ZP.

In various embodiments, the substrate-facing surface 110 of the back sheet 104 also includes at least one treated zone 118 having one or more surface treatments applied thereto. The treated zone 118 is releasably joined in facing relation with a respective adhesive zone 114 to define an adhesive protected condition. This configuration protects the adhesive 116 from contamination prior to use but allows the adhesive zone 114 to be readily released from the treated zone 118 when ready to use.

Figure 9:
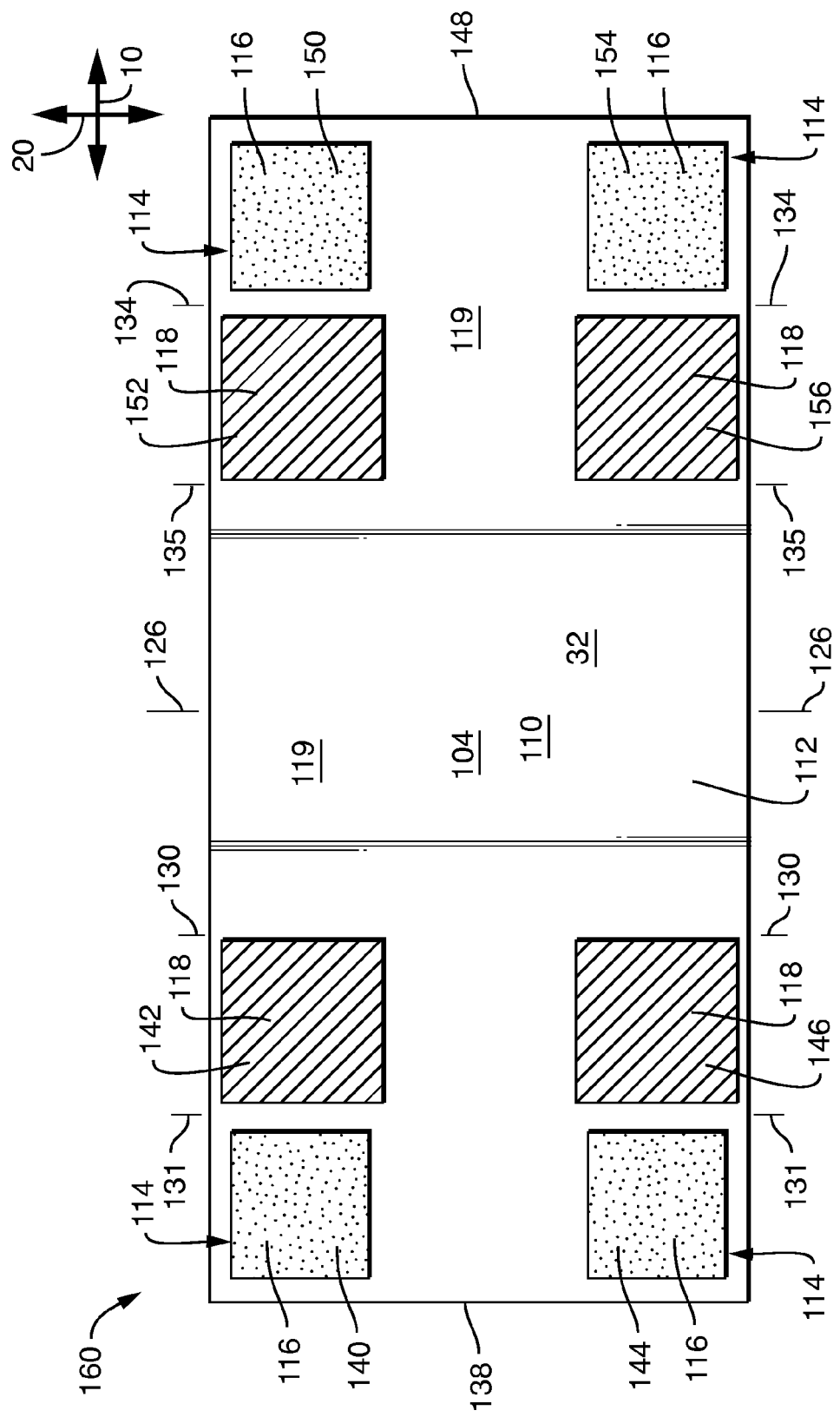
FIG. 9 is a bottom view of the absorbent article of FIG. 6 in an unfolded configuration with the substrate-facing surface towards the viewer.

In some embodiments, the substrate-facing surface 110 of the back sheet 104 includes one, two, three, four, or more zones that have been treated. For example, FIG. 9 illustrates four treated zones 118 positioned generally adjacent the adhesive zones 114 of the substrate-facing surface 110 of the back sheet 104. The treated zones are localized and are separated from other treated zones by areas of the back sheet that have not been treated in the same manner. In various embodiments, the treated zones 118 are applied to the substrate-facing surface 110 of the back sheet 104 using any suitable process and/or release agent to render the back sheet more releasable in the treated areas as compared to the untreated areas 119. For example, one or more of the treated zones 118 may be coated with silicone to reduce the force needed to separate the adhesive zone 114 from the treated zone 118 and thus transition the absorbent article from the adhesive protected condition to the adhesive application condition. In some embodiments, the treated zones 118 may be defined by localized application of silicone to reduce the force needed to separate the adhesive zone 114 from the treated zone 118. Other suitable coatings may include polytetrafluoroethylene.

In various embodiments, any suitable silicone or silicone blend may be utilized to define the treated zones 118. In various embodiments, the silicone may be applied using any suitable technique, such as, spraying, slot coating, printing, dipping, and the like, and combinations thereof. In various embodiments, the silicone may be applied in any suitable concentration to achieve the desired level of adhesive release.

In various embodiments, the treated zones 118 may cover about 10-50 percent of the substrate-facing surface 110 of the back sheet 104. In some embodiments, the treated zones may cover about 20 percent of the substrate-facing surface 110 of the back sheet 104. In various embodiments, the treated zones may have a treated zone surface area and the adhesive zones may have an adhesive zone surface area that is less than the treated zone surface area. In various embodiments, the treated zone surface area may be 100 to 150%, 100 to 125%, or 100 to 115% the adhesive zone surface area. In some embodiments, the treated zone surface area may be at least 105% the adhesive zone surface area to better ensure the entire adhesive zone surface area is aligned within the treated zone surface area.

In the embodiment of FIG. 9, each treated zone 118 has a substantially rectangular shape. It is contemplated, however, that each of the treated zones 118 may have any suitable shape and/or size. For example, in some embodiments, each treated zone 118 has a substantially triangular shape like illustrated in FIGS. 16 and 22. It is also contemplated that the treated zones 118 can be applied to the substrate-facing surface 110 of the back sheet 104 in an intermittent pattern (e.g., strips, dots) or continuous pattern. In various embodiments, the treated zones may have a shape that is the same as the shape of the adhesive zones. In other embodiments, the treated zones may have a shape that is different than the shape of the adhesive zones.

The absorbent articles described herein are folded to protect the adhesive from contamination prior to use. Specifically, the absorbent articles are folded along at least one fold line such that at least one adhesive zone is aligned in facing relation with at least one treated zone. In use, the absorbent articles are unfolded to release the adhesive zones from the treated zones and to expose the adhesive zones for attachment to the desired substrate.

Figure 6:
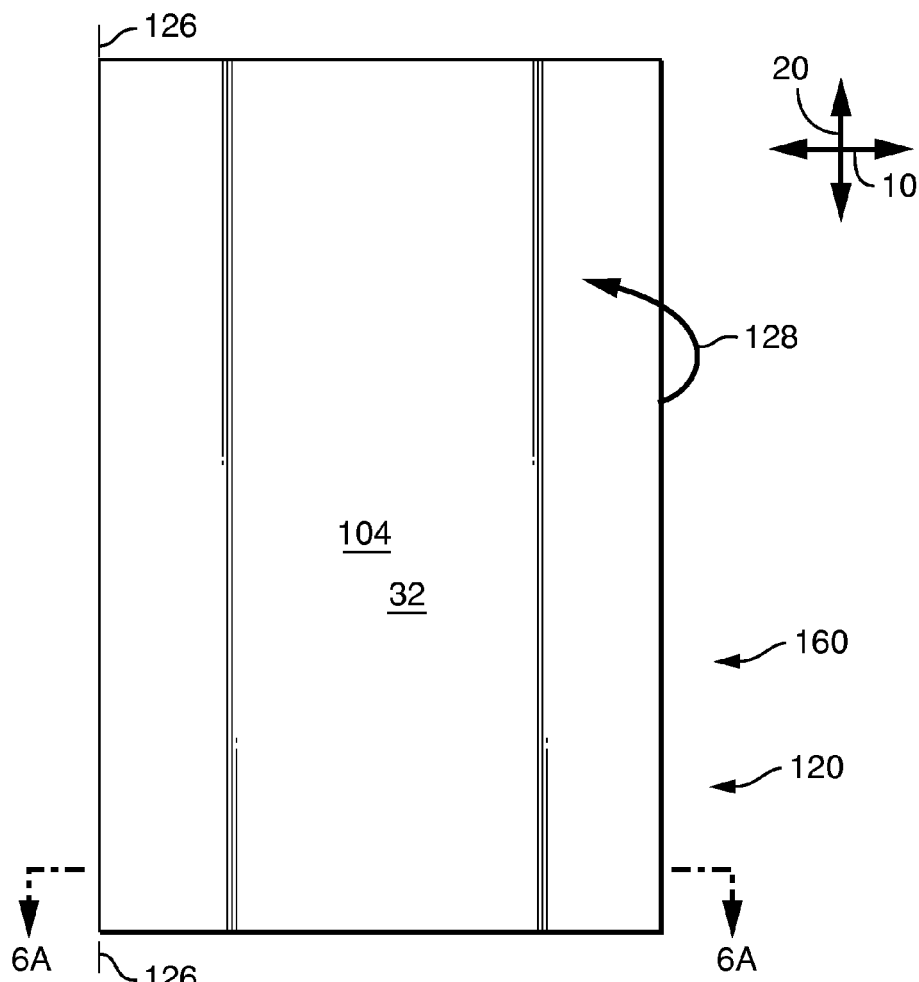
FIG. 6 is a top view of another exemplary disposable absorbent article in a first folded configuration.
Figure 6A:
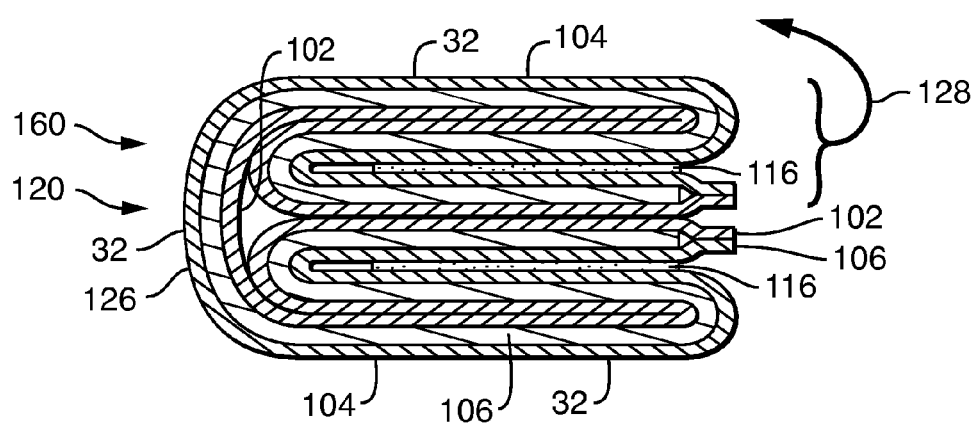
FIG. 6A is a cross-section view of the absorbent article of FIG. 6 taken along the line 6A-6A.

Referring now to FIGS. 6-9, another exemplary absorbent article 160 is illustrated in various folded and unfolded configurations. In use, the absorbent article 160 may be presented to the user in any suitable configuration. In some embodiments, the absorbent article 160 may be presented to the user in a first folded configuration 120 as illustrated in FIGS. 6 and 6A wherein FIG. 6A is a cross-sectional view of the absorbent article 160 in the first folded configuration 120 and taken along the line 6A-6A. To use, the absorbent article 160 is unfolded along a first fold line 126 in the direction indicated by the arrow 128.

Figure 7:
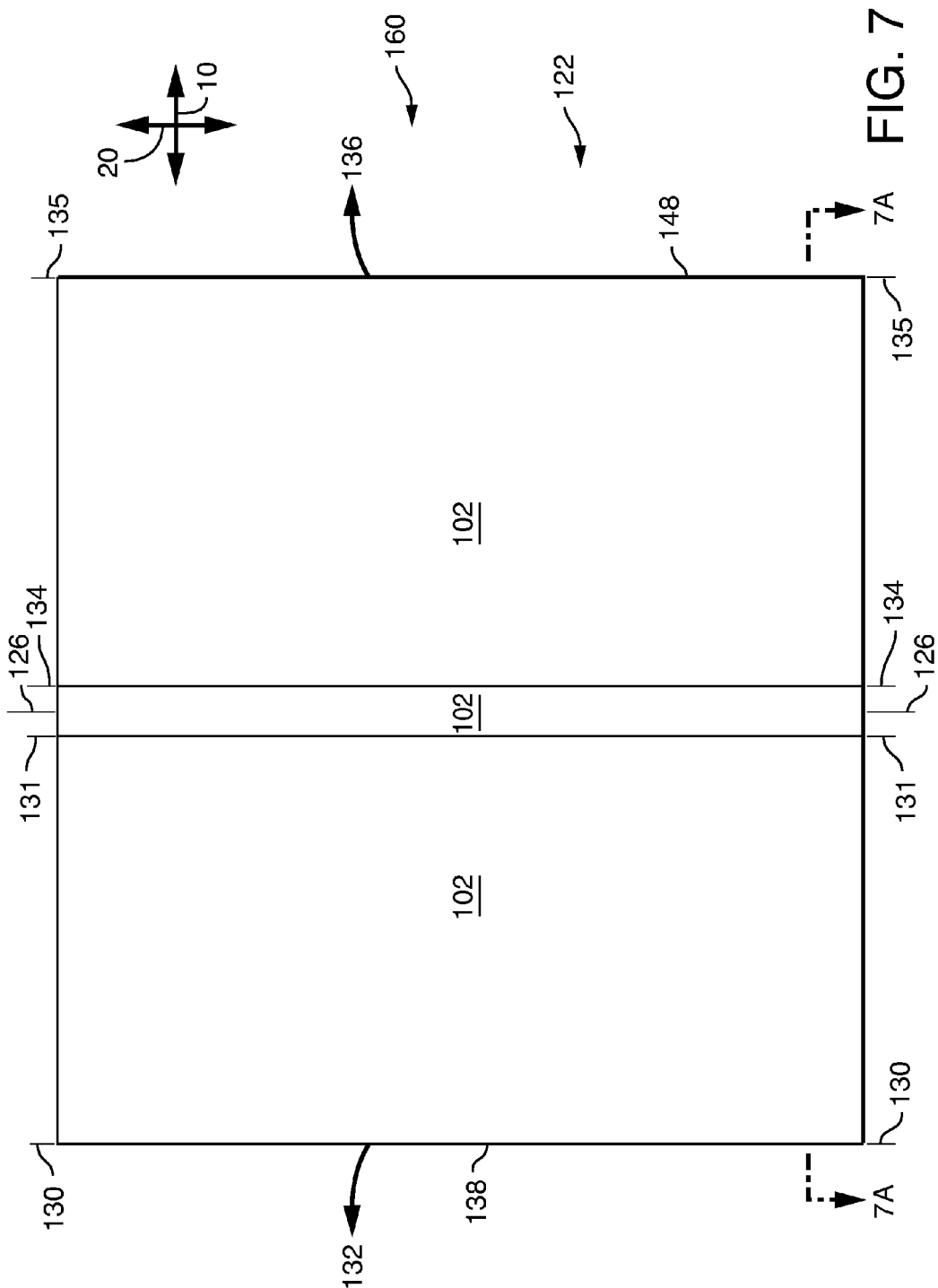
FIG. 7 is a top view of the absorbent article of FIG. 6 in a second folded configuration.
Figure 7A:
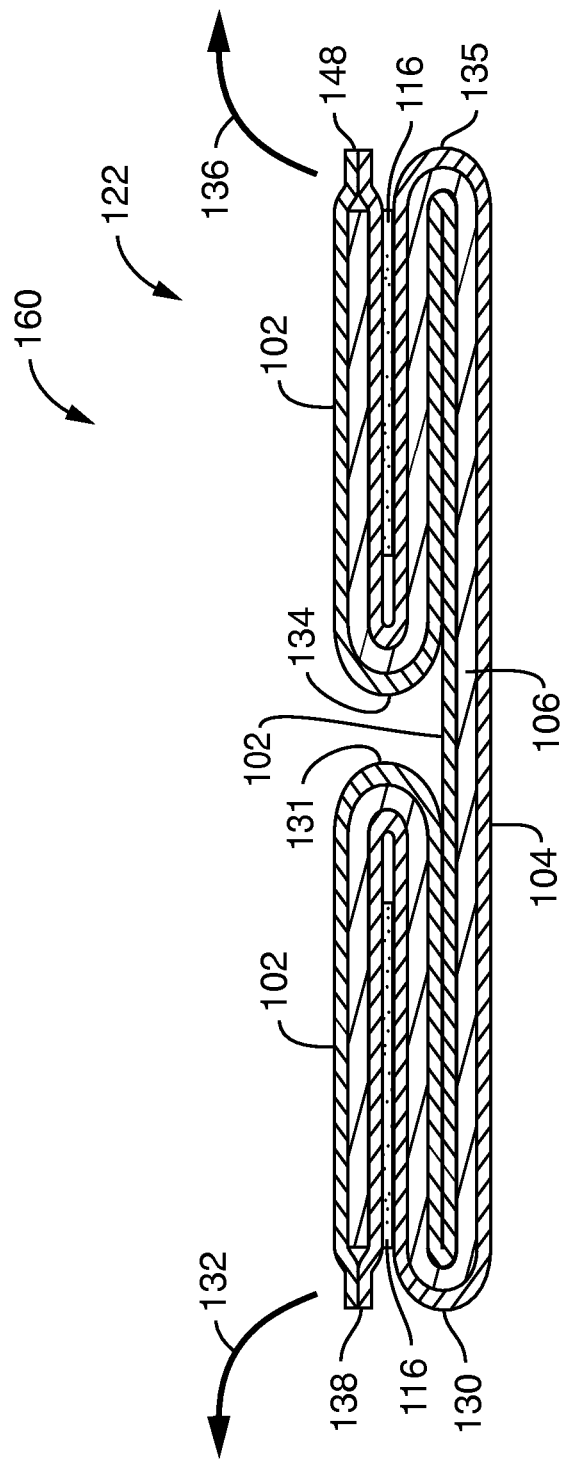
FIG. 7A is a cross-section view of the absorbent article of FIG. 7 taken along the line 7A-7A.

The partially unfolded absorbent article 160 is now in a second folded configuration 122 as illustrated in FIGS. 7 and 7A. FIG. 7A is a cross-sectional view of the absorbent article 160 of FIG. 7 in the second folded configuration 122 and taken along the line 7A-7A. The absorbent article 160 is next unfolded along a second fold line 130 and a third fold line 131 by moving the edge 138 in the direction indicated by the arrow 132. Unfolding the absorbent article 160 along the second fold line 130 and the third fold line 131 separates the first adhesive zone 140 from the first treated zone 142 and also separates the second adhesive zone 144 from the second treated zone 146 (FIG. 9). The first adhesive zone 140 and the second adhesive zone 144 are now exposed and ready for securement to any suitable substrate like the bed 101 as illustrated in FIG. 5.

The absorbent article 160 is next unfolded along a fourth fold line 134 and a fifth fold line 135 by moving the edge 148 in the direction indicated by the arrow 136. Unfolding the absorbent article 160 along the fourth fold line 134 and the fifth fold line 135 separates the third adhesive zone 150 from the third treated zone 152 and also separates the fourth adhesive zone 154 from the fourth treated zone 156 (FIG. 9). The third adhesive zone 150 and the fourth adhesive zone 154 are now exposed and ready for securement to any suitable substrate like the bed 101 as illustrated in FIG. 5.

Figure 8:
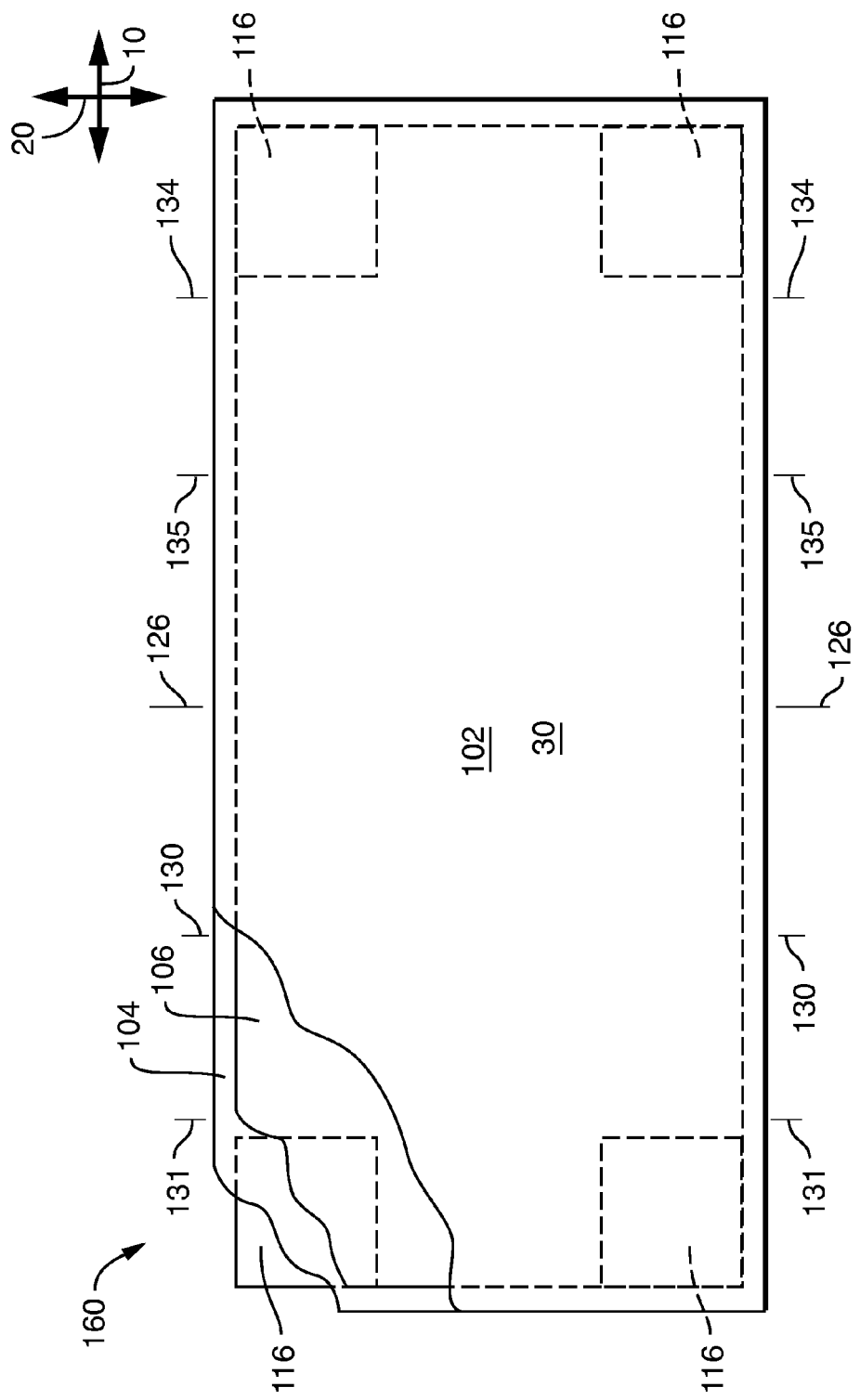
FIG. 8 is a top view of the absorbent article of FIG. 6 in an unfolded configuration with the body-facing surface towards the viewer and with portions cut away to illustrate the underlying structure.

Referring now to FIG. 8, the absorbent article 160 is illustrated in an unfolded configuration with the body-facing surface 30 towards the viewer. Portions of the absorbent article 160 are cut away to illustrate the underlying structure. The absorbent article 160 includes a top sheet 102, a back sheet 104 and an absorbent structure 106 disposed between the top sheet and the back sheet. In the illustrated embodiment, the top sheet 102 and back sheet 104 extend beyond the periphery of the absorbent structure 106 and are adhesively bonded to each other to capture the absorbent structure. The absorbent article 160 also includes adhesive zones 116 on the substrate-facing surface 32 (FIG. 9) of the absorbent article 160.

Referring now to FIG. 9, the absorbent article 160 is illustrated in an unfolded configuration with the substrate-facing surface 32 of the absorbent article 160 towards the viewer. The back sheet 104 of the absorbent article 160 includes a first adhesive zone 140, a second adhesive zone 144, a third adhesive zone 150, and a fourth adhesive zone 154. Each of the adhesive zones includes adhesive 116 applied thereto. The back sheet 104 of the absorbent article 160 also includes a first treated zone 142, a second treated zone 146, a third treated zone 152, and a fourth treated zone 156. The absorbent article 160 is folded along fold line 131 such that first adhesive zone 140 is in facing relation with first treated zone 142 and second adhesive zone 144 is in facing relation with second treated zone 146. Likewise, the absorbent article 160 is folded along fold line 134 such that third adhesive zone 150 is in facing relation with third treated zone 152 and fourth adhesive zone 154 is in facing relation with fourth treated zone 156. This alignment of adhesive zones and treated zones protects the adhesive during packaging, transport, and storage but allows the adhesive to be utilized when necessary without the use of one or more separate release sheets. Numerous alternative folds are also possible in combination with this embodiment. For example, the absorbent article 160 may additionally be folded to fully envelope the top sheet 102 and thus help keep the body-facing surface clean as illustrated in FIGS. 6 and 6A. Additional folds are also contemplated while still maintaining complete protection of the body-facing surface 30 of the absorbent article 160.

As seen in FIG. 9, the absorbent article 160 is folded multiple times in a direction essentially parallel with the lateral direction 20. However, in various embodiments, the absorbent article may be additionally or alternatively folded in a direction essentially parallel with the longitudinal direction. For example, the absorbent article 160 illustrated in FIG. 6 may be folded one or more additional times along a line that is essentially parallel with the longitudinal direction 10.

In various embodiments, the first adhesive zone 140 and the second adhesive zone 144 may be combined into a single adhesive zone extending along a first edge of the absorbent article 160 (not shown). Likewise, the third adhesive zone 150 and the fourth adhesive zone 154 may be combined into a single adhesive zone extending along a second edge, opposite the first edge, of the absorbent article 160 (not shown). In yet other embodiments, the first adhesive zone 140 and the third adhesive zone 150 may be combined into a single adhesive zone extending along a third edge of the absorbent article 160 (not shown). Likewise, the second adhesive zone 144 and the fourth adhesive zone 154 may be combined into a single adhesive zone extending along a fourth edge, opposite the third edge, of the absorbent article 160 (not shown). In each of these alternative embodiments, the treated zones may also be combined and oriented to accommodate face to face alignment with the respective adhesive zones.

Referring now to FIGS. 10-16, another exemplary absorbent article 170 is illustrated in various folded and unfolded configurations. In various embodiments, the absorbent article 170 may be presented to the user in any suitable folded or unfolded configuration. In some embodiments, the absorbent article 170 is presented to the user in a first folded configuration 171 as illustrated in FIG. 10. To use, the absorbent article 170 is unfolded along a first fold line 172 in the direction indicated by the arrow 173.

The partially unfolded absorbent article 170 is now in a second folded configuration 174 as illustrated in FIG. 11. The absorbent article 170 is next unfolded along a second fold line 175 by moving the edge 176 in the direction indicated by the arrow 177. The partially unfolded absorbent article 170 is now in a third folded configuration 178 as illustrated in FIG. 12. The absorbent article 170 is next unfolded along a third fold line 179 by moving the edge 180 in the direction indicated by the arrow 181. Consecutively or simultaneously, the absorbent article 170 is unfolded along a fourth fold line 182 by moving the corner 183 in the direction indicated by the arrow 184. Likewise, consecutively or simultaneously, the absorbent article 170 is unfolded along a fifth fold line 185 by moving the corner 186 in the direction indicated by the arrow 187.

Unfolding the absorbent article 170 along the fourth fold line 182 and the fifth fold line 185 separates the first adhesive zone 204 from the first treated zone 206 and also separates the second adhesive zone 208 from the second treated zone 210 (FIG. 16). The first adhesive zone 204 and the second adhesive zone 208 are now exposed and ready for securement to any suitable substrate like the bed 101 as illustrated in FIG. 5.

Figure 14:
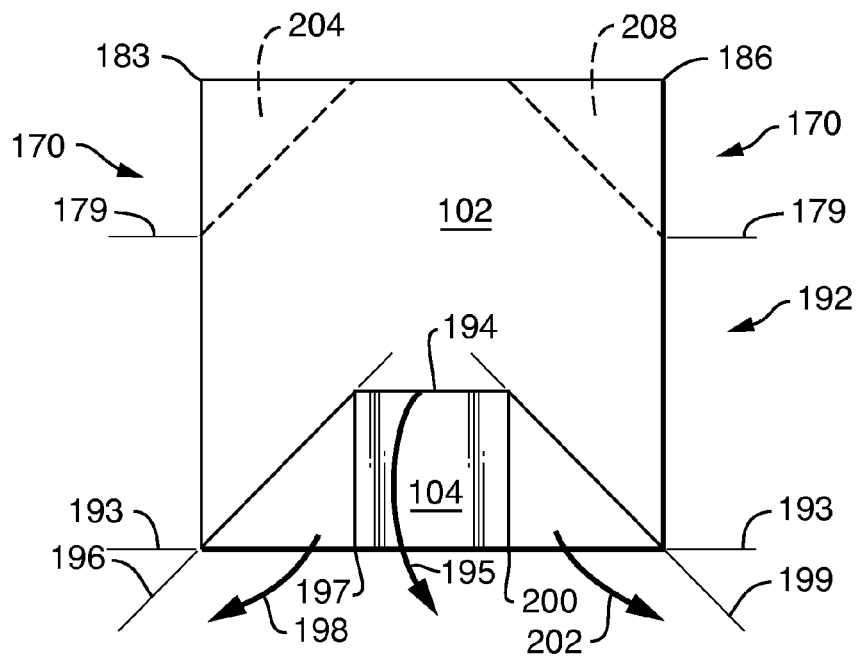
FIG. 14 is a top view of the absorbent article of FIG. 10 in a fifth folded configuration.

The partially unfolded absorbent article 170 is now in a fourth folded configuration 188 as illustrated in FIG. 13. The absorbent article 170 is next unfolded along a sixth fold line 189 by moving the edge 190 in the direction indicated by the arrow 191. The partially unfolded absorbent article 170 is now in a fifth folded configuration 192 as illustrated in FIG. 14.

The absorbent article 170 is next unfolded along a seventh fold line 193 by moving the edge 194 in the direction indicated by the arrow 195. Consecutively or simultaneously, the absorbent article 170 is unfolded along an eighth fold line 196 by moving the corner 197 in the direction indicated by the arrow 198. Likewise, consecutively or simultaneously, the absorbent article 170 is unfolded along a ninth fold line 199 by moving the corner 200 in the direction indicated by the arrow 202.

Unfolding the absorbent article 170 along the fold line 193 and the fold line 196 separates the third adhesive zone 212 from the third treated zone 214 and also separates the fourth adhesive zone 216 from the fourth treated zone 218 (FIG. 16). The third adhesive zone 212 and the fourth adhesive zone 216 are now exposed and ready for securement to any suitable substrate like the bed 101 as illustrated in FIG. 5.

Figure 15:
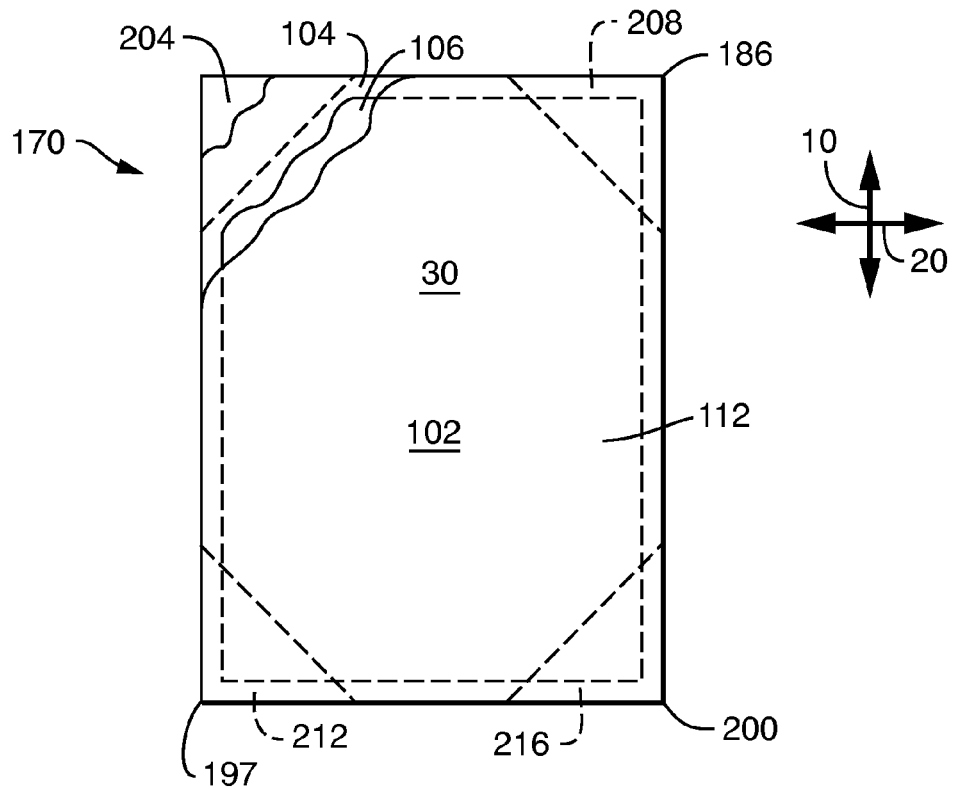
FIG. 15 is a top view of the absorbent article of FIG. 10 in an unfolded configuration with the body-facing surface towards the viewer and with portions cut away to illustrate the underlying structure.

Referring now to FIG. 15, the absorbent article 170 is illustrated in an unfolded configuration with the body-facing surface 30 towards the viewer. Portions of the absorbent article 170 are cut away to illustrate underlying structure. The absorbent article 170 includes a top sheet 102, a back sheet 104 and an absorbent structure 106 disposed between the top sheet and the back sheet. In the illustrated embodiment, the top sheet 102 and back sheet 104 extend beyond the periphery of the absorbent structure 106 and are adhesively bonded to each other to capture the absorbent structure. The absorbent article 170 also includes adhesive zones 116 on the substrate-facing surface of the back sheet 104 (FIG. 16).

Referring now to FIG. 16, the absorbent article 170 is illustrated in an unfolded configuration with the substrate-facing surface 32 towards the viewer. The back sheet 104 of the absorbent article 170 includes a first adhesive zone 204, a second adhesive zone 208, a third adhesive zone 212, and a fourth adhesive zone 216. Each of the adhesive zones includes adhesive 116 applied thereto. The back sheet 104 of the absorbent article 170 also includes a first treated zone 206, a second treated zone 210, a third treated zone 214, and a fourth treated zone 218.

The absorbent article 170 is folded along fold line 182 such that first adhesive zone 204 is in facing relation with first treated zone 206. The absorbent article 170 is also folded along fold line 185 such that second adhesive zone 208 is in facing relation with second treated zone 210. Likewise, the absorbent article 170 is also folded along fold line 196 such that third adhesive zone 212 is in facing relation with third treated zone 214. Finally, the absorbent article 170 is folded along fold line 199 such that the fourth adhesive zone 216 is in facing relation with fourth treated zone 218. This alignment of adhesive zones and treated zones keeps the adhesive protected during packaging, transport, and storage but allows the adhesive to be utilized when necessary without the use of one or more separate release sheets. Numerous alternative folds are also possible in combination with this embodiment. For example, the absorbent article 170 may additionally be folded to help keep the body-facing surface 30 clean by completely enveloping the top sheet 102 within the back sheet 104 (as illustrated in FIG. 10) until the absorbent article 170 is unfolded.

Figure 17:
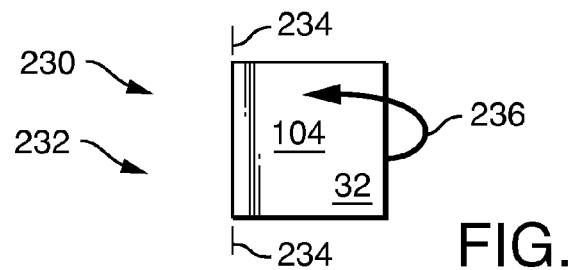
FIG. 17 is a top view of another exemplary absorbent article in a first folded configuration.

Referring now to FIGS. 17-22, another exemplary absorbent article 230 is illustrated in various folded and unfolded configurations. In use, the absorbent article 230 may be presented to the user in any suitable folded or unfolded configuration. In the illustrated embodiment, the absorbent article 230 is presented to the user in a first folded configuration 232 as shown in FIG. 17. To use, the absorbent article 230 is unfolded along a first fold line 234 in the direction indicated by the arrow 236.

Figure 18:
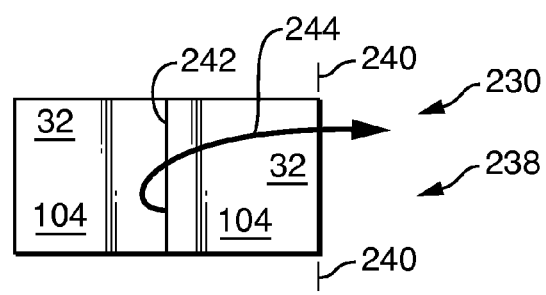
FIG. 18 is a top view of the absorbent article of FIG. 17 in a second folded configuration.
Figure 19:
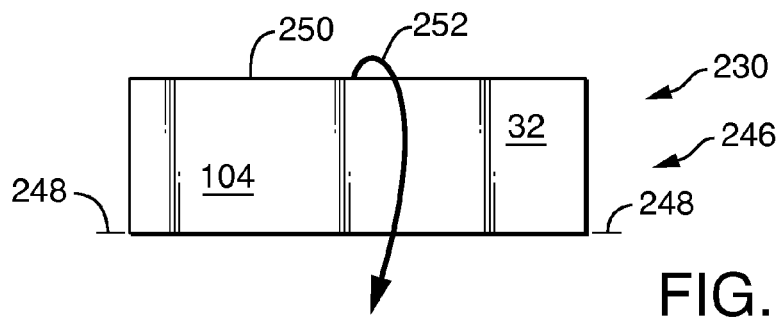
FIG. 19 is a top view of the absorbent article of FIG. 17 in a third folded configuration.

The partially unfolded absorbent article 230 is now in a second folded configuration 238 as illustrated in FIG. 18. The absorbent article 230 is next unfolded along a second fold line 240 by moving the edge 242 in the direction indicated by the arrow 244. The partially unfolded absorbent article 230 is now in a third folded configuration 246 as illustrated in FIG. 19. The absorbent article 230 is next unfolded along a third fold line 248 by moving the edge 250 in the direction indicated by the arrow 252. The absorbent article 230 is now in a fourth folded configuration 254 as illustrated in FIG. 20.

Consecutively or simultaneously, the absorbent article 230 is unfolded along a fourth fold line 256 and a fifth fold line 258 by moving the corner 260 in the direction indicated by the arrow 262. Likewise, consecutively or simultaneously, the absorbent article 230 is unfolded along the fourth fold line 256 and a sixth fold line 264 by moving the corner 266 in the direction indicated by the arrow 268.

Unfolding the absorbent article 230 along the fifth fold line 258 separates the first adhesive zone 270 from the first treated zone 272 (FIG. 22). Unfolding the absorbent article 230 along the sixth fold line 264 separates the second adhesive zone 274 from the second treated zone 276 (FIG. 22). The first adhesive zone 270 and the second adhesive zone 274 are now exposed and ready for securement to any suitable substrate like the bed 101 as illustrated in FIG. 5.

Figure 20:
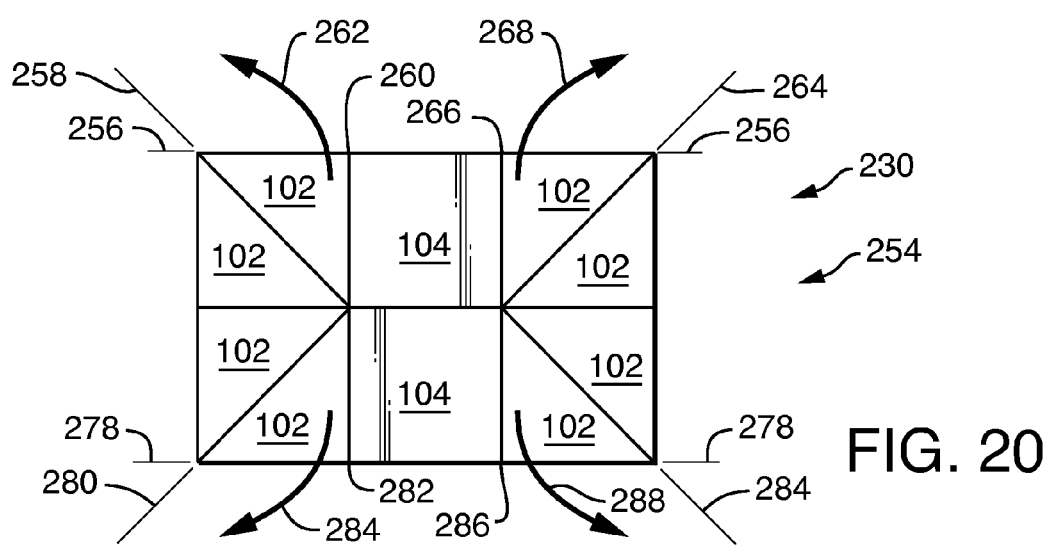
FIG. 20 is a top view of the absorbent article of FIG. 17 in a fourth folded configuration.

Still referring to FIG. 20, consecutively or simultaneously with other steps, the absorbent article 230 is unfolded along a seventh fold line 278 and an eighth fold line 280 by moving the corner 282 in the direction indicated by the arrow 284. Likewise, consecutively or simultaneously, the absorbent article 230 is unfolded along the seventh fold line 278 and a ninth fold line 284 by moving the corner 286 in the direction indicated by the arrow 288.

Unfolding the absorbent article 230 along the eighth fold line 280 separates the third adhesive zone 290 from the third treated zone 292 (FIG. 22). Unfolding the absorbent article 230 along the ninth fold line 284 separates the fourth adhesive zone 294 from the fourth treated zone 296 (FIG. 22). The third adhesive zone 290 and the fourth adhesive zone 294 are now exposed and ready for securement to any suitable substrate like the bed 101 as illustrated in FIG. 5.

Figure 21:
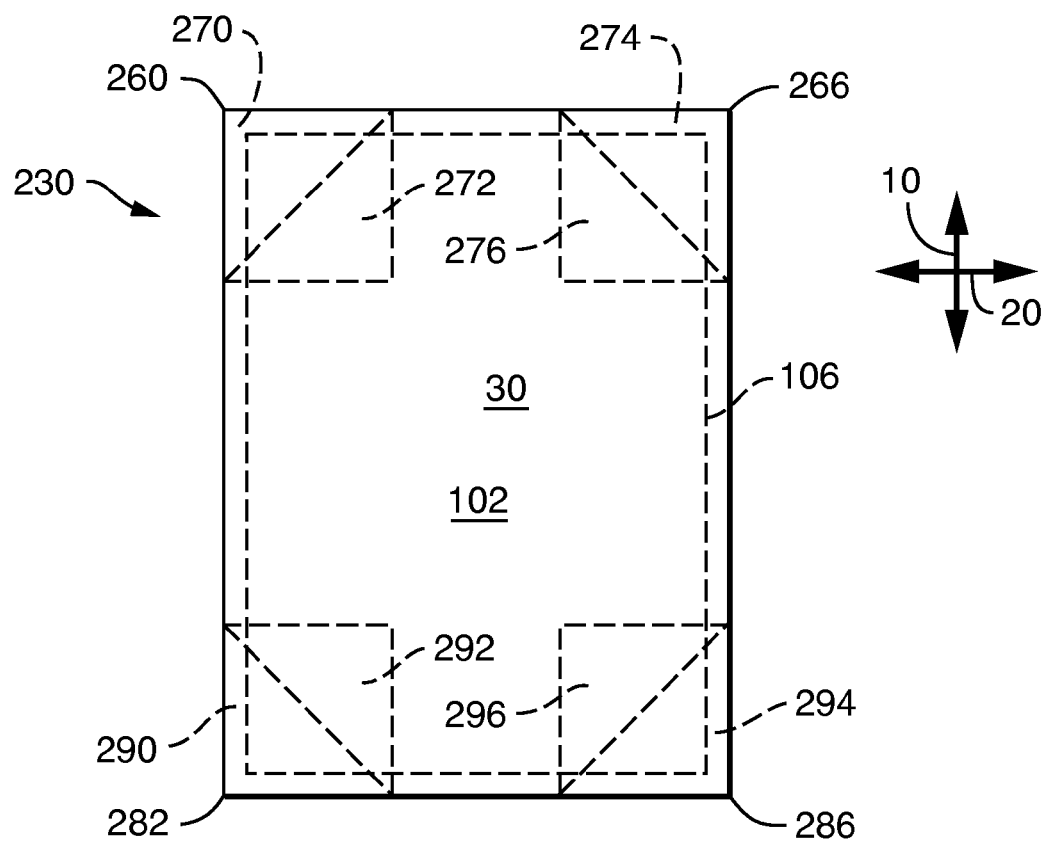
FIG. 21 is a top view of the absorbent article of FIG. 17 in an unfolded configuration with the body-facing surface towards the viewer.

Referring now to FIG. 21, the absorbent article 230 is illustrated in an unfolded configuration with the body-facing surface 30 towards the viewer. The absorbent article 230 includes a top sheet 102, a back sheet 104 (FIG. 22) and an absorbent structure 106 disposed between the top sheet and the back sheet. In the illustrated embodiment, the top sheet 102 and back sheet 104 extend beyond the periphery of the absorbent structure 106 and are adhesively bonded to each other to capture the absorbent structure.

Referring now to FIG. 22, the absorbent article 230 is illustrated in an unfolded configuration with the substrate-facing surface 32 towards the viewer. The back sheet 104 of the absorbent article 230 includes a first adhesive zone 270, a second adhesive zone 274, a third adhesive zone 290, and a fourth adhesive zone 294. Each of the adhesive zones include adhesive 116 applied thereto. The back sheet 104 of the absorbent article 230 also includes a first treated zone 272, a second treated zone 276, a third treated zone 292, and a fourth treated zone 296.

The absorbent article 230 is folded along fold line 258 such that first adhesive zone 270 is in facing relation with first treated zone 272. The absorbent article 230 is also folded along fold line 264 such that second adhesive zone 274 is in facing relation with second treated zone 276. Likewise, the absorbent article 230 is also folded along fold line 280 such that third adhesive zone 290 is in facing relation with third treated zone 292. Finally, the absorbent article 230 is folded along fold line 284 such that the fourth adhesive zone 294 is in facing relation with the fourth treated zone 296. This alignment of adhesive zones and treated zones keeps the adhesive protected during packaging, transport, and storage but allows the adhesive to be utilized when necessary without the use of one or more separate release sheets. Numerous alternative or additional folds are also possible in combination with this embodiment.

In various embodiments, the absorbent articles of the present invention may be folded about fold lines that are parallel with the lateral direction 20 and/or folded about fold lines that are parallel with the longitudinal direction 10, and/or folded about fold lines that are parallel with neither the lateral direction 20 nor the longitudinal direction 10 (i.e., non-parallel). For example, the absorbent article 160 illustrated in FIG. 9 includes fold lines 126, 130, 131, 134, and 135 that are parallel with the lateral direction 20. In another example, the absorbent article 170 illustrated in FIG. 16 includes fold lines 172 and 175 that are parallel with the longitudinal direction 10, fold lines 179, 189, and 193 that are parallel with the lateral direction 20, and fold lines 182, 185, 196, and 199 that are parallel with neither the longitudinal direction 10 nor the lateral direction 20 (i.e., non-parallel with the longitudinal direction 10 or the lateral direction 20). In yet another example, the absorbent article 230 illustrated in FIG. 22 includes fold lines 234 and 240 that are parallel with the longitudinal direction 10, fold lines 248, 256, and 278 that are parallel with the lateral direction 20, and fold lines 258, 264, 280, and 284 that are parallel with neither the longitudinal direction 10 nor the lateral direction 20 (i.e., are non-parallel with the longitudinal direction 10 or the lateral direction 20).

Figure 23:
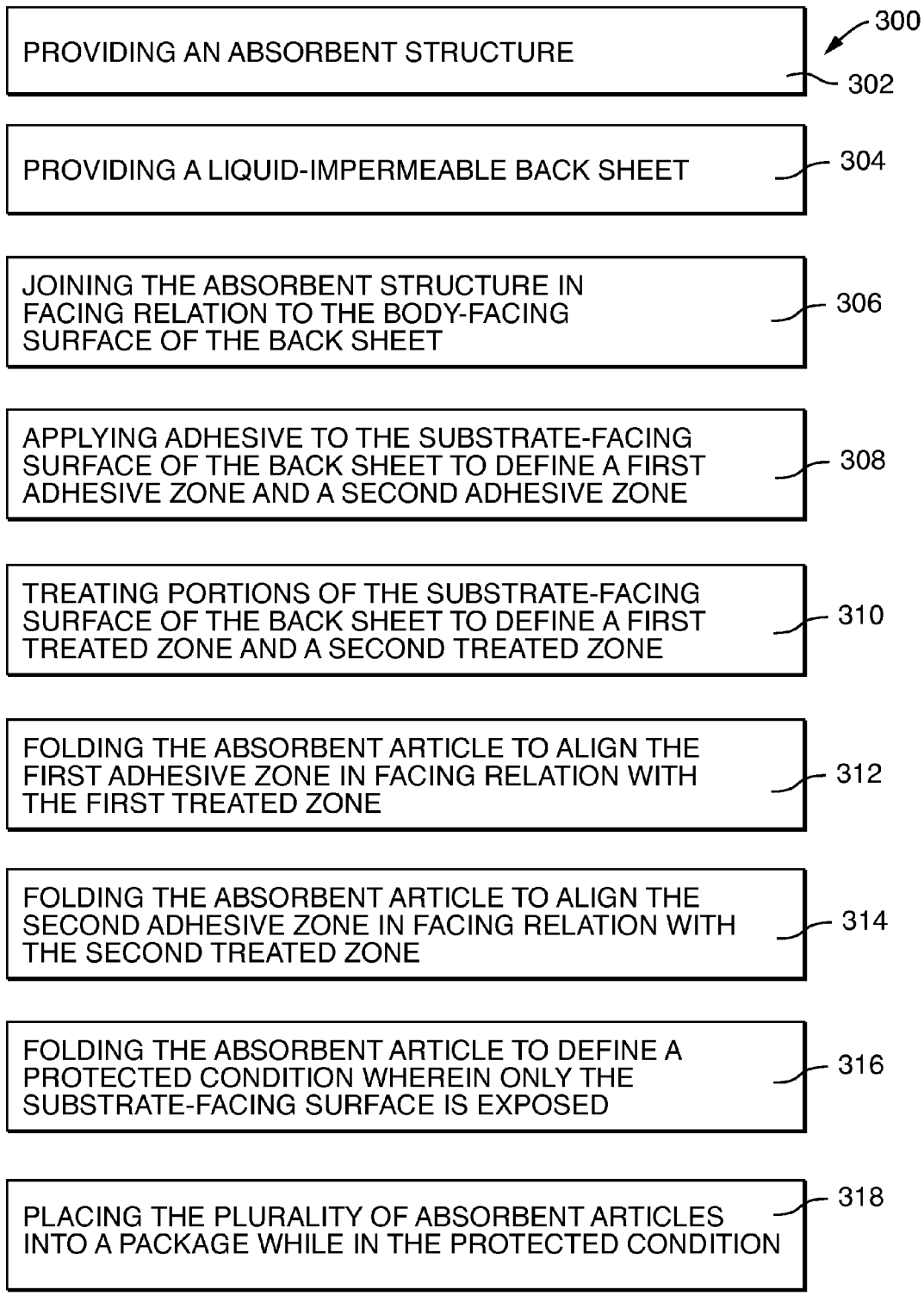
FIG. 23 is a flow chart illustration of an exemplary method of the present invention.

The absorbent articles of the present invention can be made using any suitable method. In some embodiments, the absorbent articles of the present invention may be made using a method 300 as illustrated in FIG. 23. The method 300 includes the step 302 of providing an absorbent structure. The method 300 further includes the step 304 of providing a liquid-impermeable back sheet. The back sheet defines a body-facing surface and a substrate-facing surface. The method 300 also includes the step 306 of joining the absorbent structure in facing relation to the body-facing surface of the back sheet to define an absorbent article.

The method 300 further includes the step 308 of applying adhesive to the substrate-facing surface of the back sheet to define a first adhesive zone and a second adhesive zone like those described herein. The method 300 further includes the step 310 of treating portions of the substrate-facing surface of the back sheet to define a first treated zone and a second treated zone like those described herein. The method 300 further includes the step 312 of folding the absorbent article to align the first adhesive zone in facing relation with the first treated zone. Finally, the method 300 includes the step 314 of folding the absorbent article to align the second adhesive zone in facing relation with the second treated zone.

In some embodiments, the method 300 may further include the step 316 of folding the absorbent article to define a protected condition wherein only the substrate-facing surface of the absorbent article is exposed. For example, FIG. 6 illustrates the absorbent article 160 wherein only the substrate-facing surface 32 is exposed. Likewise, FIG. 10 illustrates the absorbent article 170 with only the substrate-facing surface 32 exposed. Finally, FIGS. 17, 18, and 19 illustrate the absorbent article 230 in various configurations wherein only the substrate-facing surface 32 is exposed. In these embodiments, the body-facing surface 30 is completely folded within the substrate-facing surface 32. This configuration may help protect the body-facing surface 30 from contamination prior to use and may help protect the adhesive from contamination prior to use.

In some embodiments, the method 300 may include repeating steps 302 through 316 to provide a plurality of absorbent articles in the protected condition. The method 300 may also include the step 318 of placing the plurality of absorbent articles into a package while in the protected condition.

Figure 24:
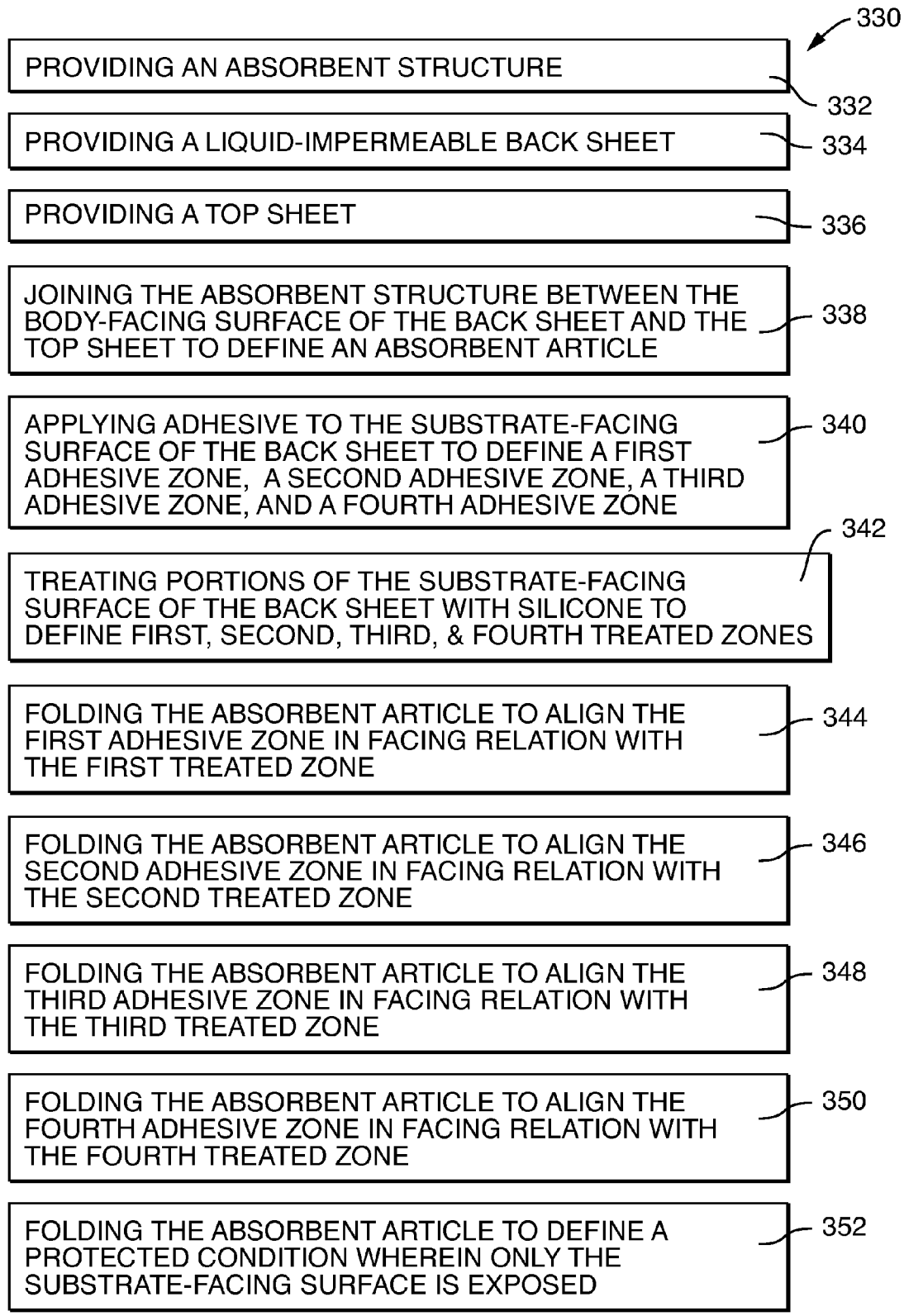
FIG. 24 is a flow chart illustration of another exemplary method of the present invention.

In another embodiment, the absorbent articles of the present invention may be made using a method 330 as illustrated in FIG. 24. The method 330 includes the step 332 of providing an absorbent structure. In some embodiments, the step 332 may include providing an absorbent structure having a mixture of cellulose fibers and superabsorbent particles intermixed therein. The method 330 may further include the step 334 of providing a liquid-impermeable back sheet having a body-facing surface and a substrate-facing surface. In some embodiments, the step 334 may include providing a back sheet made of polyethylene film. In other embodiments, the step 334 may include providing a back sheet made of polyethylene film laminated with a nonwoven facing layer.

The method 330 may further include the step 336 of providing a top sheet. In some embodiments, the step 336 may include providing a top sheet made of nonwoven spunbond polymer. The method 330 may further include the step 338 of joining the absorbent structure between the body-facing surface of the back sheet and the top sheet to define an absorbent article.

The method 330 may further include the step 340 of applying adhesive to the substrate-facing surface of the back sheet to define a first adhesive zone, a second adhesive zone, a third adhesive zone, and a fourth adhesive zone. In various embodiments, the step 340 may include applying adhesive to the substrate-facing surface of the back sheet using a pressure sensitive hot melt adhesive. In some embodiments, the pressure sensitive hot melt adhesive may be applied using any suitable method such as slot coat, swirl, melt blowing, bead, printing, or the like, or combinations thereof. In some embodiments, the hot melt adhesive is applied using a slot coat adhesive applicator at any suitable concentration to achieve the desired peel force.

The method 330 also includes the step 342 of treating portions of the substrate-facing surface of the back sheet. In some embodiments, the step 342 may include treating portions of the substrate-facing surface of the back sheet with silicone to define a first treated zone, a second treated zone, a third treated zone, and a fourth treated zone. In various embodiments, the silicone may be applied to the back sheet using any suitable method such as slot coat, swirl, melt blown, bead, printing, or the like, or combination thereof. In some embodiments the silicone is applied using spray nozzles at any suitable concentration to achieve the desired release characteristics.

The method 330 also includes the step 344 of folding the absorbent article to align the first adhesive zone in facing relation with the first treated zone, the step 346 of folding the absorbent article to align the second adhesive zone in facing relation with the second treated zone, the step 348 of folding the absorbent article to align the third adhesive zone in facing relation with the third treated zone, and the step 350 of folding the absorbent article to align the fourth adhesive zone in facing relation with the fourth treated zone.

The method 330 also includes the step 352 of folding the absorbent article to define a protected condition wherein only the substrate-facing surface is exposed. In some embodiments, the steps 344, 346, 348, and/or 350 may include folding the absorbent article along a first line that is parallel to the longitudinal direction of the absorbent article or folding the absorbent article along a second line that is parallel to the lateral direction of the absorbent article. In some embodiments, the steps 344, 346, 348, and/or 350 may include folding the absorbent article along a first line that is neither parallel to the longitudinal direction nor the lateral direction.

In some embodiments, at least one of the steps 344, 346, 348, and/or 350 may include folding the absorbent article along a first line that is parallel to the longitudinal direction of the absorbent article or folding the absorbent article along a second line that is parallel to the lateral direction of the absorbent article and at least one of the steps 344, 346, 348, and/or 350 may include folding the absorbent article along a third line that is neither parallel to the longitudinal direction nor the lateral direction.

In various embodiments, the adhesive 116 is configured to provide a shear strength between the disposable absorbent articles and the substrate of between about 1,500 grams per square inch and about 3,500 grams per square inch. Suitably, the adhesive 116 is configured to provide a shear strength between about 2,000 grams per square inch and about 3,000 grams per square inch. More suitably, the adhesive 116 is configured to provide a shear strength between about 2,200 grams per square inch and about 2,500 grams per square inch as measured relative to cotton sheets using a 2 inch by 6 inch sample of adhesive coated polyethylene. The samples are rolled with a 2 kg weight and then pulled apart in shear at a rate of 20 inches/min. The samples are pulled apart in shear until a break occurs or the poly releases from the cotton fabric. The results are normalized to provide a force per square inch equivalent.

It is contemplated that the disposable absorbent articles can be adapted to provide the shear strength between the article and the substrate in other suitable ways in addition to adhesive. For example, the articles can include mechanical fasteners (e.g., hook and loop fasteners, slot and tab, magnets) to provide suitable shear strength between the articles and the substrates. In another suitable example, the back sheet 104 of the articles can comprise a high coefficient of friction material.

In some embodiments, the adhesive 116 is also configured to provide a peel strength between the absorbent articles and the bed sheet 103 when the absorbent article is adhered to the bed sheet between about 200 grams per inch and about 500 grams per inch. In some embodiments, the adhesive 116 is configured to provide a peel strength between about 250 grams per inch and about 450 grams per inch. In other embodiments, the adhesive 116 is configured to provide a peel strength between about 300 grams per inch and about 350 grams per inch as measured relative to cotton sheets using a 2 inch by 6 inch sample of adhesive coated polyethylene. The samples are rolled with a 2 kg weight and then pulled apart in peel at a rate of 20 inches/min. The samples are pulled apart in peel until a break occurs or the poly releases from the cotton fabric. The results are normalized to provide a force per square inch equivalent.

The attachment between the absorbent structure 106 and the top sheet 102 and/or the back sheet 104 may have an internal cohesive force of between about 45 grams per square inch and about 100 grams per square inch. Suitably, the attachment between the absorbent structure 106 and the top sheet 102 and/or the back sheet 104 may have an internal cohesive force between about 55 grams per square inch and about 80 grams per square inch, more suitably, about 64 grams per square inch.

While the invention has been described in detail with respect to specific embodiments thereof, it will be appreciated that those skilled in the art, upon attaining understanding of the foregoing will readily appreciate alterations to, variations of, and equivalents to these embodiments. Accordingly, the scope of the present invention should be assessed as that of the appended claims and any equivalents thereto. Additionally, all combinations and/or sub-combinations of the disclosed embodiments, ranges, examples, and alternatives are also contemplated.

The invention claimed is:

1. An absorbent article comprising,
    a back sheet having a body-facing surface and a substrate-facing surface,
    an absorbent structure joined in facing relation with the body-facing surface of the back sheet to define the absorbent article,
    the substrate-facing surface of the back sheet comprising an adhesive zone and a treated zone, and
    the absorbent article being folded along a fold line such that the adhesive zone and the treated zone are aligned in facing relation.

2. The absorbent article of claim 1 wherein the absorbent article defines a longitudinal direction and a lateral direction perpendicular to the longitudinal direction and wherein the fold line is parallel with either the lateral direction or the longitudinal direction.

3. The absorbent article of claim 1 wherein the absorbent article defines a longitudinal direction and a lateral direction perpendicular to the longitudinal direction and wherein the fold line is non-parallel with either the lateral direction or the longitudinal direction.

4. The absorbent article of claim 1 wherein the back sheet comprises,
    a first adhesive zone, a second adhesive zone, a first treated zone, and a second treated zone each positioned on the substrate-facing surface,
    the absorbent article being folded along a first fold line such that the first adhesive zone and the first treated zone are aligned in facing relation, and
    the absorbent article being folded along a second fold line such that the second adhesive zone and the second treated zone are aligned in facing relation.

5. The absorbent article of claim 4 wherein the absorbent article is folded at a third fold line to position the body-facing surface in a protected condition.

6. The absorbent article of claim 5 wherein the absorbent article is folded at a third fold line to position the first adhesive zone and the second adhesive zone in a protected condition.

7. The absorbent article of claim 4 wherein the first adhesive zone and the second adhesive zone comprise pressure sensitive hot melt adhesive having a concentration between 10 and 60 grams per square meter.

8. The absorbent article of claim 4 wherein the first treated zone and the second treated zone comprise silicone.

9. The absorbent article of claim 4 wherein the back sheet comprises,
    a first adhesive zone, a second adhesive zone, a third adhesive zone, a fourth adhesive zone, a first treated zone, a second treated zone, a third treated zone, and a fourth treated zone, each on the substrate-facing surface,
    the absorbent article being folded along a first fold line such that the first adhesive zone and the first treated zone are aligned in facing relation and the second adhesive zone and the second treated zone are aligned in facing relation, and
    the absorbent article being folded along a second fold line such that the third adhesive zone and the third treated zone are aligned in facing relation and the fourth adhesive zone and the fourth treated zone are aligned in facing relation.

10. A method of making a folded absorbent article comprising,
    providing an absorbent structure, providing a liquid-impermeable back sheet having a body-facing surface and a substrate-facing surface, joining the absorbent structure in facing relation to the body-facing surface of the back sheet to define an absorbent article, applying adhesive to the substrate-facing surface of the back sheet to define a first adhesive zone and a second adhesive zone, treating portions of the substrate-facing surface of the back sheet to define a first treated zone and a second treated zone, folding the absorbent article to align the first adhesive zone in facing relation with the first treated zone, and folding the absorbent article to align the second adhesive zone in facing relation with the second treated zone.

11. The method of claim 10 further comprising, folding the absorbent article to define a protected condition wherein only the substrate-facing surface is exposed.

12. The method of claim 11 further comprising repeating the steps to provide a plurality of absorbent articles in the protected condition and placing the plurality of absorbent articles into a package while in the protected condition.

13. The method of claim 10 wherein the treating step includes applying silicone to the substrate-facing surface of the back sheet to define the first treated zone and the second treated zone.

14. The method of claim 10 wherein the absorbent article defines a longitudinal direction and a lateral direction and wherein the folding step includes folding the absorbent article along a first line that is parallel to the longitudinal direction or folding the absorbent article along a second line that is parallel to the lateral direction.

15. The method of claim 10 wherein the absorbent article defines a longitudinal direction and a lateral direction and wherein the folding step includes folding the absorbent article along a first line that is neither parallel to the longitudinal direction nor the lateral direction.

16. The method of claim 14 wherein the folding step includes folding the absorbent article along a third line that is neither parallel to the longitudinal direction nor the lateral direction.

17. A method of making a folded absorbent article comprising, providing an absorbent structure, providing a liquid-impermeable back sheet made of polyethylene film and having a body-facing surface and a substrate-facing surface, joining the absorbent structure in facing relation to the body-facing surface of the back sheet to define an absorbent article, applying adhesive to the substrate-facing surface of the back sheet to define a first adhesive zone, a second adhesive zone, a third adhesive zone, and a fourth adhesive zone, treating portions of the substrate-facing surface of the back sheet with silicone to define a first treated zone, a second treated zone, a third treated zone, and a fourth treated zone, folding the absorbent article to align the first adhesive zone in facing relation with the first treated zone, folding the absorbent article to align the second adhesive zone in facing relation with the second treated zone, folding the absorbent article to align the third adhesive zone in facing relation with the third treated zone, folding the absorbent article to align the fourth adhesive zone in facing relation with the fourth treated zone, and folding the absorbent article to define a protected condition wherein only the substrate-facing surface is exposed.

18. The method of claim 17 wherein the absorbent article defines a longitudinal direction and a lateral direction and wherein the folding step includes folding the absorbent article along a first line that is parallel to the longitudinal direction or folding the absorbent article along a second line that is parallel to the lateral direction.

19. The method of claim 17 wherein the absorbent article defines a longitudinal direction and a lateral direction and wherein the folding step includes folding the absorbent article along a first line that is neither parallel to the longitudinal direction nor the lateral direction.

20. The method of claim 18 wherein the folding step includes folding the absorbent article along a third line that is neither parallel to the longitudinal direction nor the lateral direction.

* * * * *